US009687180B1

(12) United States Patent
Deninger et al.

(10) Patent No.: US 9,687,180 B1
(45) Date of Patent: Jun. 27, 2017

(54) INTELLIGENT HUMAN MOTION SYSTEMS AND METHODS

(71) Applicant: Yotta Navigation Corporation, Santa Clara, CA (US)

(72) Inventors: William James Deninger, San Mateo, CA (US); Andrew John Zaydak, Sunnyvale, CA (US); Joseph Martin Schlesselman, Santa Clara, CA (US)

(73) Assignee: YOTTA NAVIGATION CORPORATION, Santa Clara, CA (US)

( * ) Notice: Subject to any disclaimer, the term of this patent is extended or adjusted under 35 U.S.C. 154(b) by 0 days.

(21) Appl. No.: 14/983,441

(22) Filed: Dec. 29, 2015

Related U.S. Application Data

(60) Provisional application No. 62/127,794, filed on Mar. 3, 2015.

(51) Int. Cl.
  *A61B 5/11* (2006.01)
  *A61B 5/00* (2006.01)
  (Continued)

(52) U.S. Cl.
  CPC .......... *A61B 5/1123* (2013.01); *A61B 5/6823* (2013.01); *A61B 5/6831* (2013.01);
  (Continued)

(58) Field of Classification Search
  USPC .......... 701/409, 532; 73/1.77; 702/160, 150
  See application file for complete search history.

(56) References Cited

U.S. PATENT DOCUMENTS

| 9,317,660 B2 * | 4/2016 | Burich | G06F 19/3418 |
| 2005/0033200 A1 * | 2/2005 | Soehren | A61B 5/0002 |
| | | | 600/595 |

(Continued)

OTHER PUBLICATIONS

Vo, Nhut, "Intelligent Human Motion Detection Sensor" available at https://sbirsource.com/sbir/topics/85317-intelligent-human-motion-detection-sensor, last viewed Jul. 11, 2016.

(Continued)

*Primary Examiner* — Thomas Tarcza
*Assistant Examiner* — Richard Goldman
(74) *Attorney, Agent, or Firm* — Pillsbury Winthrop Shaw Pittman LLP

(57) ABSTRACT

A system for identifying human motion of a subject may comprise: a sensor platform attached to the subject; an attitude filter that receives sensor data and calculates the attitude and heading of the platform; a feature construction and aggregation unit that receives the sensor data and the attitude and heading to calculate a feature vector for a human motion model, an evaluation unit that receives feature vectors and calculates the probability that an instance of a specific human motion occurred; wherein the feature vector comprises: one or more feature constructions, X, such as: forces along and perpendicular to the gravity field direction; a magnitude of rotations perpendicular to the gravity field direction; an adjusted pressure altitude; one or more feature constructions which are time derivatives dX/dt; and one or more feature constructions which are derivatives V(dX/dt), wherein: $V(x)=2*H(x)-1$, $H(x)=+1$ ($x>0$), $0$ ($x<0$), and x is dX/dt.

24 Claims, 14 Drawing Sheets

(51) Int. Cl.
   *G01C 21/14* (2006.01)
   *G01S 19/42* (2010.01)
   *G01C 5/06* (2006.01)
(52) U.S. Cl.
   CPC ............. *A61B 5/725* (2013.01); *G01C 5/06* (2013.01); *G01C 21/14* (2013.01); *G01S 19/42* (2013.01); *A61B 2562/0219* (2013.01)

(56) References Cited

U.S. PATENT DOCUMENTS

| | | | | |
|---|---|---|---|---|
| 2007/0260418 | A1* | 11/2007 | Ladetto ................ | G01C 21/165 702/150 |
| 2010/0121227 | A1* | 5/2010 | Stirling ................ | A61B 5/1127 600/595 |
| 2010/0274481 | A1* | 10/2010 | Krishnaswamy .... | G01C 21/165 701/532 |
| 2012/0254934 | A1* | 10/2012 | McBrearty .......... | G06F 19/3481 725/118 |
| 2013/0041590 | A1* | 2/2013 | Burich ................ | G06F 19/3418 702/19 |
| 2013/0311134 | A1* | 11/2013 | Kordari ................ | G06F 17/10 702/160 |
| 2013/0332064 | A1* | 12/2013 | Funk .................... | G01C 21/206 701/409 |
| 2015/0201867 | A1* | 7/2015 | Peindl ................. | A61B 5/1118 600/595 |
| 2015/0230735 | A1* | 8/2015 | Venkatraman ........ | A61B 5/1112 600/301 |
| 2015/0241245 | A1* | 8/2015 | Hsu ...................... | G01C 25/005 73/1.77 |
| 2015/0247729 | A1* | 9/2015 | Meduna ............... | H04W 4/027 702/150 |
| 2016/0259061 | A1* | 9/2016 | Carter .................. | G01S 19/05 |

OTHER PUBLICATIONS

Gafurov, Davrondzhon and Snekkenes, Einar, "Gait Recognition Using Wearable Motion Recording Sensors," EURASIP Journal on Advances in Signal Processing vol. 2009 (2009), Article ID 415817, 16 pages, doi: 10.1155/2009/415817; available at https//pdfs.semanticscholar.org/6757/254d27b761ada5bd88642bd0112fcb962cf.pdf, last viewed Jul. 11, 2016.

* cited by examiner

| Model Designator | Channel | | | | | | |
|---|---|---|---|---|---|---|---|
| | 1 | 2 | 3 | 4 | 5 | 6 | 7 |
| m0 | $A_x$ | $A_y$ | $A_z$ | | | | |
| m1 | $|A|$ | | | | | | |
| m2 | $\omega_x$ | $\omega_y$ | $\omega_z$ | | | | |
| m3* | $|\dot{\alpha}|$ | | | | | | |
| m4 | $A_x - Sg_x$ | $A_y - Sg_y$ | $A_z - Sg_z$ | | | | |
| m5* | $|A - Sg|$ | | | | | | |
| m6 | $A_x$ | $A_y$ | $A_z$ | $\omega_x$ | $\omega_y$ | $\omega_z$ | |
| m7 | $A_x - Sg_x$ | $A_y - Sg_y$ | $A_z - Sg_z$ | $\omega_x$ | $\omega_y$ | $\omega_z$ | |
| m8 | $d|A|$ | | | | | | |
| m9* | $|A - Sg|$ | $|\omega|$ | | | | | |
| m10* | $A \cdot Sg$ | $|A - (A \cdot \hat{Sg})\hat{Sg}|$ | | | | | |
| m11* | $A \cdot Sg$ | $|A - (A \cdot \hat{Sg})\hat{Sg}|$ | | | | | |
| m12* | $A \cdot Sg$ | $|A - (A \cdot \hat{Sg})Sg|$ | $A \cdot Sg$ | $|A - (A \cdot \hat{Sg})\hat{Sg}|$ | $\frac{dA}{dt} \cdot Sg$ | $|\frac{dA}{dt} - (\frac{dA}{dt} \cdot \hat{Sg})\hat{Sg}|$ | $dP$ |
| m13* | $\omega \cdot Sg$ | $|\omega - (\omega \cdot \hat{Sg})\hat{Sg}|$ | | | | | |

| Model Designator | 1 | 2 | 3 | 4 | 5 | 6 |
|---|---|---|---|---|---|---|
| m14* | $A \cdot Sg$ | $\|A-(A \cdot \hat{Sg})\hat{Sg}\|$ | $\|\omega \cdot Sg\|$ | $\|\omega-(\omega \cdot \hat{Sg})\hat{Sg}\|$ | | |
| m15* | $A \cdot Sg$ | $\|A-(A \cdot \hat{Sg})\hat{Sg}\|$ | $\|\omega \cdot Sg\|$ | $\|\omega-(\omega \cdot \hat{Sg})\hat{Sg}\|$ | [1][2] | [1][3] |
| m16* | $A \cdot Sg$ | $\|A-(A \cdot \hat{Sg})\hat{Sg}\|$ | $\|\omega-(\omega \cdot \hat{Sg})\hat{Sg}\|$ | [1][2] | [2][3] | |
| m17 | | deprecated | | | | |
| m18 | | deprecated | | | | |
| m19* | $A \cdot Sg$ | | | | | |
| m20* | $A \cdot Sg$ | $V\left(\frac{d}{dt}\left|A-(A \cdot \hat{Sg})\hat{Sg}\right|\right)$ | $V\left(\frac{d}{dt}\|\omega \cdot Sg\|\right)$ | $V\left(\frac{d}{dt}\|\omega-(\omega \cdot \hat{Sg})\hat{Sg}\|\right)$ | | |
| m21* | $A \cdot Sg$ | $V\left(\frac{d}{dt}(A \cdot Sg)\right)$ | $V\left(\frac{d}{dt}\|A-(A \cdot \hat{Sg})\hat{Sg}\|\right)$ | $V\left(\frac{d}{dt}\|\omega \cdot Sg\|\right)$ | $V\left(\frac{d}{dt}\|\omega-(\omega \cdot \hat{Sg})\hat{Sg}\|\right)$ | [1][2] |
| m22* | $A \cdot Sg$ | $V\left(\frac{d}{dt}(A \cdot Sg)\right)$ | $V\left(\frac{d}{dt}\|A-(A \cdot \hat{Sg})\hat{Sg}\|\right)$ | $\|\omega-(\omega \cdot \hat{Sg})\hat{Sg}\|$ | [1][3] | [2][3] |
| m23* | $A \cdot Sg$ | $\|A-(A \cdot \hat{Sg})\hat{Sg}\|$ | $\|\omega-(\omega \cdot \hat{Sg})\hat{Sg}\|$ | $V\left(\frac{d}{dt}\|\omega-(\omega \cdot \hat{Sg})\hat{Sg}\|\right)$ | | [1][3] |
| m24* | $A \cdot Sg - 1$ | $\omega \cdot Sg$ | $\|A-(A \cdot \hat{Sg})\hat{Sg}\|$ | $\|\omega-(\omega \cdot \hat{Sg})\hat{Sg}\|$ | | |
| m25* | $A \cdot Sg - 1$ | $\omega \cdot Sg$ | $\|A-(A \cdot \hat{Sg})\hat{Sg}\|$ | | [1][2] | [1][3] |
| m26* | | $(\omega \cdot Sg)(Sg \cdot S_{veh})$ | | | | |

Channel

| Model Designator | 7 | 8 | 9 | 10 | 11 | 12 | 13 | 14 |
|---|---|---|---|---|---|---|---|---|
| m14* | [1][4] | | | | | | | |
| m15* | | [2][3] | [2][4] | [3][4] | | | | |
| m16* | | | | | | | | |
| m17 | | | | | | | | |
| m18 | | | | | | | | |
| m19* | | | | | | | | |
| m20* | [2][4] | [2][5] | [3][4] | [3][5] | [4][5] | | | |
| m21* | [3][4] | [4][6] | [5][6] | | | | | |
| m22* | [4][5] | [3][5] | [2][5] | [3][4] | [2][5] | [3][4] | [3][5] | [4][5] |
| m23* | [3][4] | | | | | | | |
| m24* | | | | | | | | |
| m25* | | | | | | | | |
| m26* | | | | | | | | |

INTELLIGENT HUMAN MOTION SYSTEMS AND METHODS

CROSS-REFERENCE TO RELATED APPLICATIONS

This application claims the benefit of U.S. Provisional Application No. 62/127,794 filed Mar. 3, 2015, incorporated by reference in its entirety herein.

This application was made with U.S. Government support under Contract No. W15P7T-11-C-H225 awarded by the U.S. Department of Defense. The Government has certain rights in the invention.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE RELATED ART

This application relates generally to identifying human motion, and more particularly to intelligent human motion systems and methods.

BACKGROUND

Intelligent Human Motion (IHM) is a method of identifying, categorizing and classifying human activities/movements using input from sensors, generally including 3-axis accelerometers, gyroscopes and magnetometers; inexpensive sensor platforms are available on most cellular devices. Human movements that are desired to be identified are abundant and diverse and include, among others: walking, running, jumping, sitting down, etc. Uses of IHM include navigation, situational awareness, health, fitness, productivity and lifestyle monitoring and management, and targeted advertising. IHM has well known technical challenges, due to: (1) IHM motion classification accuracy being predicated on the location of the sensor platform on the subject; (2) if large IHM databases are to be utilized on a handheld device to obtain accurate motion classification then this requires high computational efficiency and power management; (3) IHM models are dependent on subject diversity and data volume.

There is a need for improved IHM methods to address the technical challenges.

SUMMARY

In embodiments, the methods and apparatuses described herein provide identification of different human motions, in real time and with a high degree of accuracy, as a basis for enhanced navigation, including dead reckoning, health and fitness monitoring, and situation awareness monitoring, for example.

According to some embodiments, a system for identifying human motion of a subject may comprise: a sensor platform attached to the subject, the sensor platform comprising 3-axis magnetometers, 3 axis accelerometers, 3-axis rate gyroscopes and a first memory for storing time synchronized magnetometer, accelerometer and rate gyroscope data at sample times separated by a specified time interval; an attitude filter that receives the magnetometer, accelerometer and rate gyroscope data from the sensor platform, the attitude filter comprising a processor programmed to calculate, from the magnetometer, accelerometer and rate gyroscope data, attitude and heading of the sensor platform at each of the sample times; a feature construction and aggregation unit that receives the magnetometer, accelerometer and rate gyroscope data from the sensor platform and the attitude and heading from the attitude filter, the feature construction and aggregation unit comprising a processor programmed to calculate a feature vector for a human motion model from the magnetometer, accelerometer, and rate gyroscope data and the attitude and heading, using a predefined template stored in a second memory, feature vectors for a specified number of consecutive sample times being aggregated into a frame, a plurality of the frames being generated; and an evaluation unit that receives the plurality of the frames, the evaluation unit being programmed to calculate the probability, for each one of the frames, that the feature vectors in the frame resulted from an instance of a specific human motion corresponding to the human motion model; wherein the human motion model is a model chosen from the group consisting of walking forwards, jogging, running, side stepping left, side stepping right, walking backwards, standing up, sitting down and traversing stairs, and the specific human motion is correspondingly walking forwards, jogging, running, side stepping left, side stepping right, walking backwards, standing up, sitting down and traversing stairs, respectively; wherein the feature vector comprises: one or more first feature constructions, X, comprising at least one of: a force along the gravity field direction; a magnitude of forces perpendicular to the gravity field direction; a magnitude of rotations perpendicular to the gravity field direction; an adjusted pressure altitude; one or more second feature constructions which are derivatives dX/dt, wherein dX/dt is a time derivative of one of the one or more feature constructions; and one or more third feature constructions which are derivatives V(dX/dt), wherein: $V(x)=2*H(x)-1$, and $H(x)$ is the Heaviside step function, $H(x)=+1$ ($x>0$), $0$ ($x<0$), and x is dX/dt.

According to some embodiments, a system for identifying human motion of a subject, may comprise: a sensor platform attached to the subject, the sensor platform comprising 3-axis magnetometers, 3 axis accelerometers, 3-axis rate gyroscopes and a first memory for storing time synchronized magnetometer, accelerometer and rate gyroscope data at sample times separated by a specified time interval; an attitude filter that receives the magnetometer, accelerometer and rate gyroscope data from the sensor platform, the attitude filter comprising a processor programmed to calculate, from the magnetometer, accelerometer and rate gyroscope data, attitude and heading of the sensor platform at each of the sample times; a feature construction and aggregation unit that receives the magnetometer, accelerometer and rate gyroscope data from the sensor platform and the attitude and heading from the attitude filter, the feature construction and aggregation unit comprising a processor programmed to calculate a feature vector for a human motion model from the magnetometer, accelerometer, and rate gyroscope data and the attitude and heading, using a predefined template stored in a second memory, a feature vector being calculated for each of the sample times, feature vectors for a specified number of consecutive sample times being aggregated into a frame, a plurality of the frames being generated; and an evaluation unit that receives the plurality of the frames, the evaluation unit being programmed to calculate the probability, for each one of the frames, that the feature vectors in the frame resulted from an instance of a specific human motion corresponding to the human motion model; wherein the human motion model is a model chosen from the group consisting of walking forwards, jogging and running, and the specific human motion is correspondingly walking forwards, jogging and running, respectively; wherein the feature vector comprises: a first feature construction being force, u, along the gravity field direction; a second feature construction being a magnitude, v, of forces perpendicular to the gravity field direction; a third feature construction being a magnitude, w, of rotations perpendicular to the gravity field direction; a fourth feature construction being a function, V(du/dt), where du/dt is a time derivative of the force along the gravity field direction; a fifth feature construction being a function, V(dv/dt), where dv/dt is a time derivative of the magnitude of forces perpendicular to the gravity field direction; and a sixth feature construction being a function, V(dw/dt), where dw/dt is a time derivative of the magnitude of rotations perpendicular to the gravity field direction; wherein: $V(x)=2*H(x)-1$, and $H(x)$ is the Heaviside step function, $H(x)=+1$ ($x>0$), $0$ ($x<0$).

According to some embodiments, a method of identifying human motion of a subject may comprise: acquiring time synchronized magnetometer, accelerometer and rate gyroscope data at sample times separated by a specified time interval using a sensor platform attached to the subject, the sensor platform comprising 3-axis magnetometers, 3 axis accelerometers, 3-axis rate gyroscopes and a first memory for storing the time synchronized magnetometer, accelerometer and rate gyroscope data; calculating attitude and heading of the sensor platform at each of the sample times at an attitude filter unit comprising a filter and a processor, by manipulating the magnetometer, accelerometer and rate gyroscope data received from the memory; calculating a feature vector for a human motion model at a feature construction and aggregation unit comprising a processor programmed to calculate the feature vector for a walking forwards model from the magnetometer, accelerometer, and rate gyroscope data received from the first memory and the attitude and heading received from the attitude filter unit, using a predefined template stored in a second memory, a feature vector being calculated for each of the sample times, feature vectors for a specified number of consecutive sample times being aggregated into a frame, a plurality of the frames being generated; and calculating the probability, at an evaluation unit, for each one of the plurality of the frames, that the feature vectors in the frame resulted from an instance of a specific human motion corresponding to the human motion model; wherein the human motion model is a model chosen from the group consisting of walking forwards, jogging and running, and the specific human motion is correspondingly walking forwards, jogging and running, respectively; wherein the feature vector comprises: a first feature construction being force, u, along the gravity field direction; a second feature construction being a magnitude, v, of forces perpendicular to the gravity field direction; a third feature construction being a magnitude, w, of rotations perpendicular to the gravity field direction; a fourth feature construction being a function, V(du/dt), where du/dt is a time derivative of the force along the gravity field direction; a fifth feature construction being a function, V(dv/dt), where dv/dt is a time derivative of the magnitude of forces perpendicular to the gravity field direction; and a sixth feature construction being a function, V(dw/dt), where dw/dt is a time derivative of the magnitude of rotations perpendicular to the gravity field direction; wherein: $V(x)=2*H(x)-1$, and $H(x)$ is the Heaviside step function, $H(x)=+1$ ($x>0$), $0$ ($x<0$).

According to some embodiments, a dead reckoning system for a human subject travelling on foot may comprise: a system for identifying human motion of walking forwards of a subject as described herein; an event processing unit that receives the probability, for each one of the frames, that the feature vectors in the frame resulted from an instance of walking forwards from the evaluation unit, the event processing unit comprising a processor programmed to qualify a walking forwards event; a GPS event unit that receives GPS positional data, the GPS event unit comprising a processor programmed to calculate the position of the dead reckoning system from the GPS positional data; a database unit comprising a memory device, the database unit storing subject parameters, the subject parameters comprising an average step length of the subject, and GPS positional data received from the GPS event unit; and a navigation update unit that receives notification of qualified walking forwards events and retrieves subject parameters and GPS positional data from the database unit, the navigation update unit comprising a processor programmed to calculate a navigation update relative to a last known position determined by the GPS positional data.

According to some embodiments, a system for identifying human motion of walking forwards of a subject may comprise: a sensor platform attached to the subject, the sensor platform comprising 3-axis magnetometers, 3 axis accelerometers, 3-axis rate gyroscopes and a memory for storing time synchronized magnetometer, accelerometer and rate gyroscope data at sample times separated by a specified time interval; an attitude filter that receives the magnetometer, accelerometer and rate gyroscope data from the sensor platform, the attitude filter comprising a processor programmed to calculate, from the magnetometer, accelerometer and rate gyroscope data, attitude and heading of the sensor platform at each of the sample times; a feature construction unit that receives the magnetometer, accelerometer and rate gyroscope data from the sensor platform and the attitude and heading from the attitude filter, the feature construction unit comprising a processor programmed to calculate feature vectors for each of the sample times for a walking forwards human motion model from the magnetometer, accelerometer, and rate gyroscope data and the attitude and heading; and an evaluation unit that receives the feature vectors, the evaluation unit being programmed to calculate the probability that the feature vectors resulted from an instance of the human motion of walking forwards; wherein each of the feature vectors comprise: one or more first feature constructions, X, comprising: a force along the gravity field direction; a magnitude of forces perpendicular to the gravity field direction; and a magnitude of rotations perpendicular to the gravity field direction; one or more second feature constructions which are derivatives dX/dt, wherein dX/dt is a time derivative of one of the one or more feature constructions X; and one or more third feature constructions which are derivatives V(dX/dt), wherein: $V(x)=2*H(x)-1$, and $H(x)$ is the Heaviside step function, $H(x)=+1$ ($x>0$), $0$ ($x<0$), and x is dX/dt.

BRIEF DESCRIPTION OF THE DRAWINGS

These and other aspects and features will become apparent to those ordinarily skilled in the art upon review of the following description of specific embodiments of the invention in conjunction with the accompanying figures, in which:

Figure 5D:
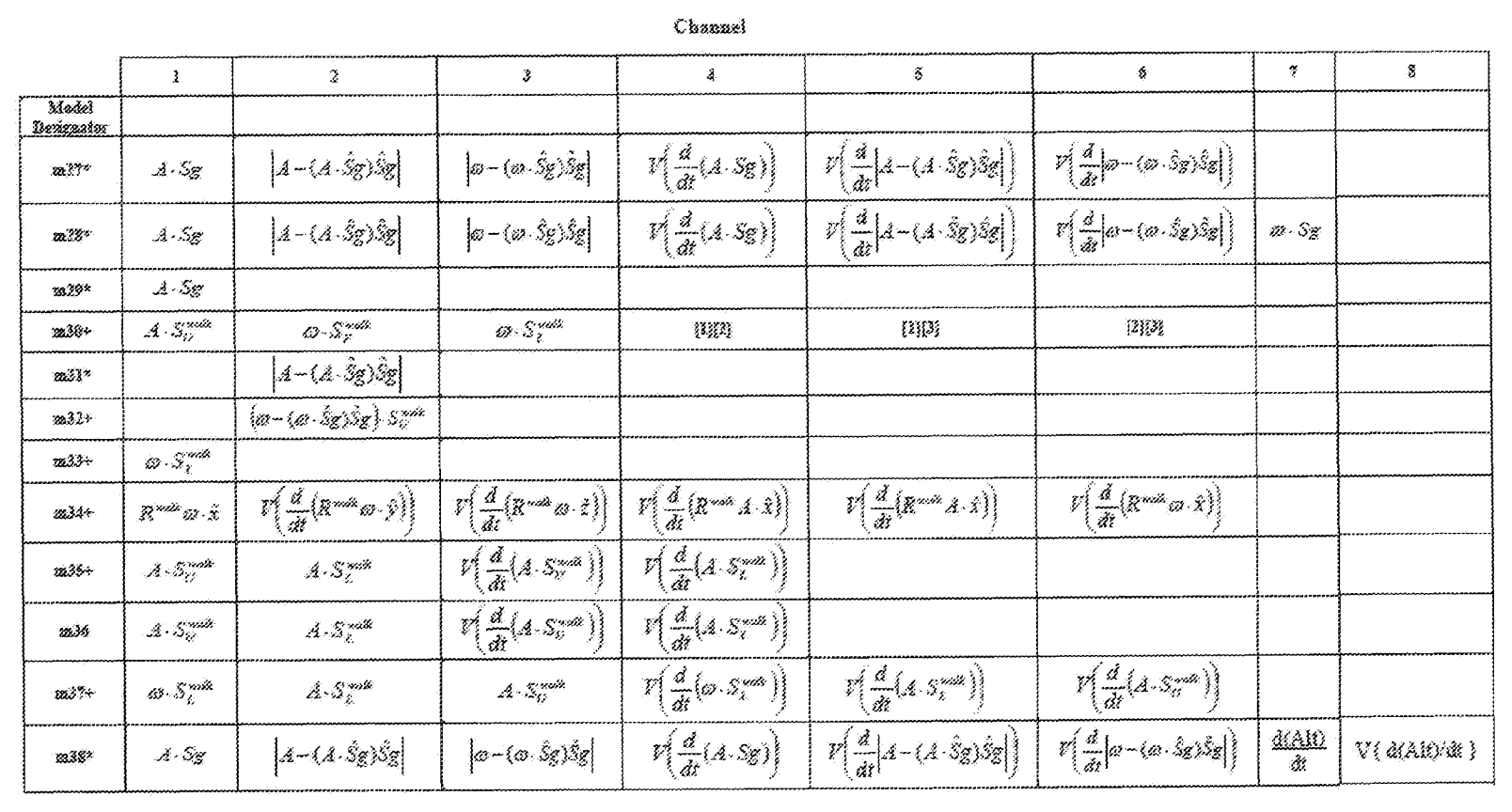

FIGS. 5A-5D depict a table showing different IMU data utilized in 36 different IHM feature constructions, according to one embodiment.

DETAILED DESCRIPTION

For the purposes of explanation, numerous specific details are set forth throughout this description in order to provide a thorough understanding. It will be appreciated, however, by persons skilled in the art that the embodiments described herein may be practiced without some of these specific details. In other instances, well-known structures and devices are shown in block diagram form to avoid obscuring the underlying principles of the various embodiments.

Figure 1:
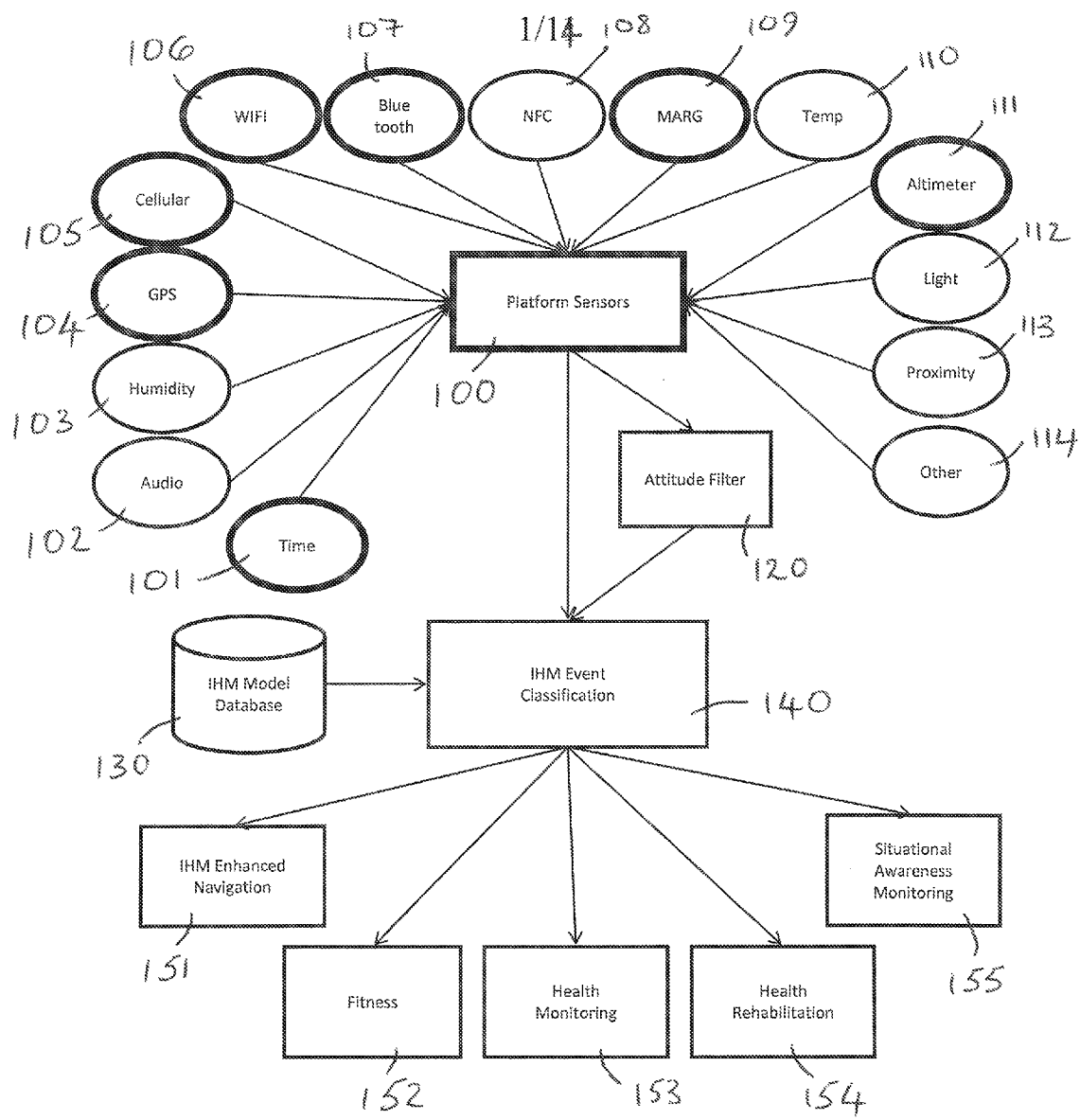
FIG. 1 depicts an IHM system block diagram 10, according to one embodiment.
Figure 2:
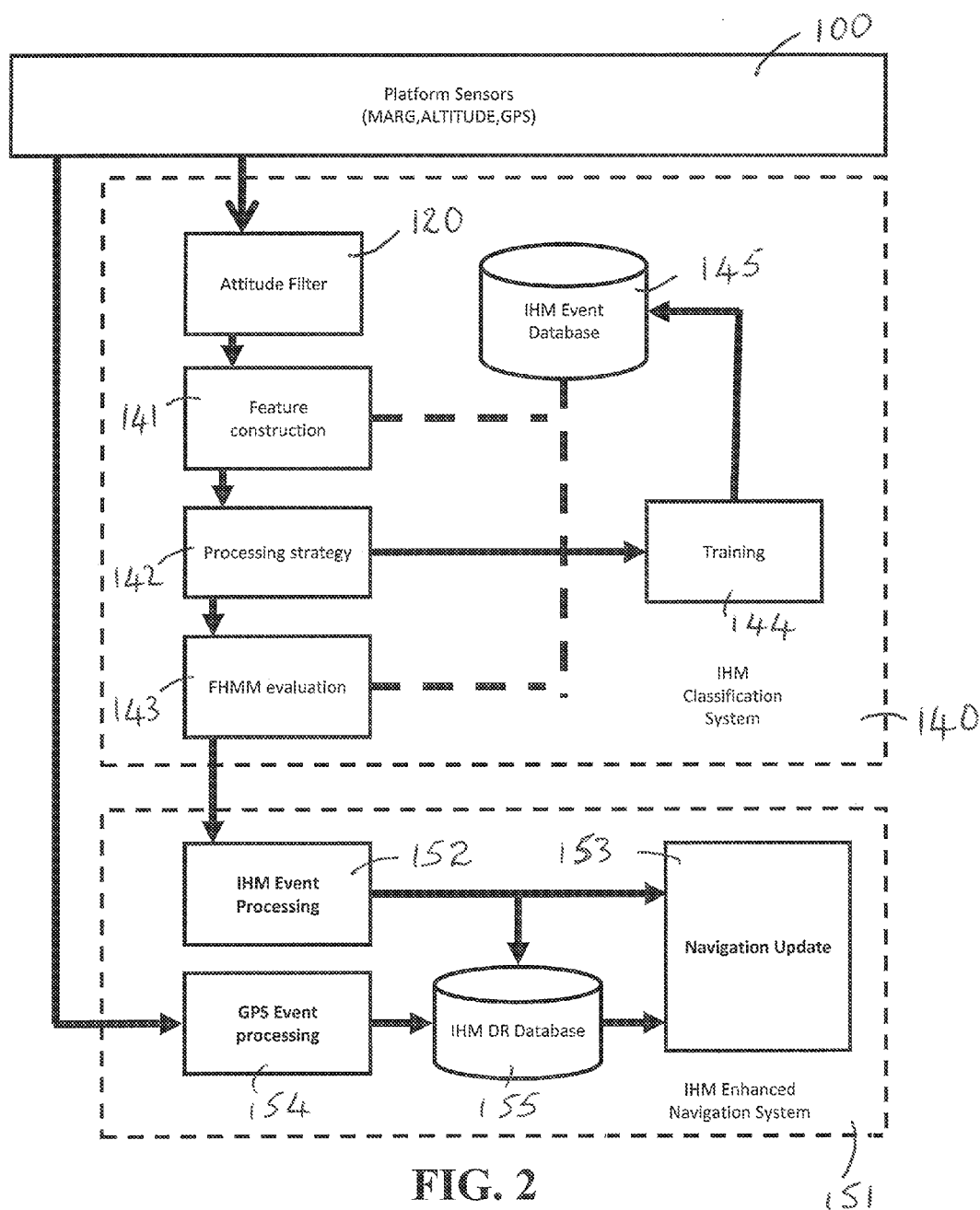
FIG. 2 depicts details of the system of FIG. 1, according to one embodiment.
Figure 3:
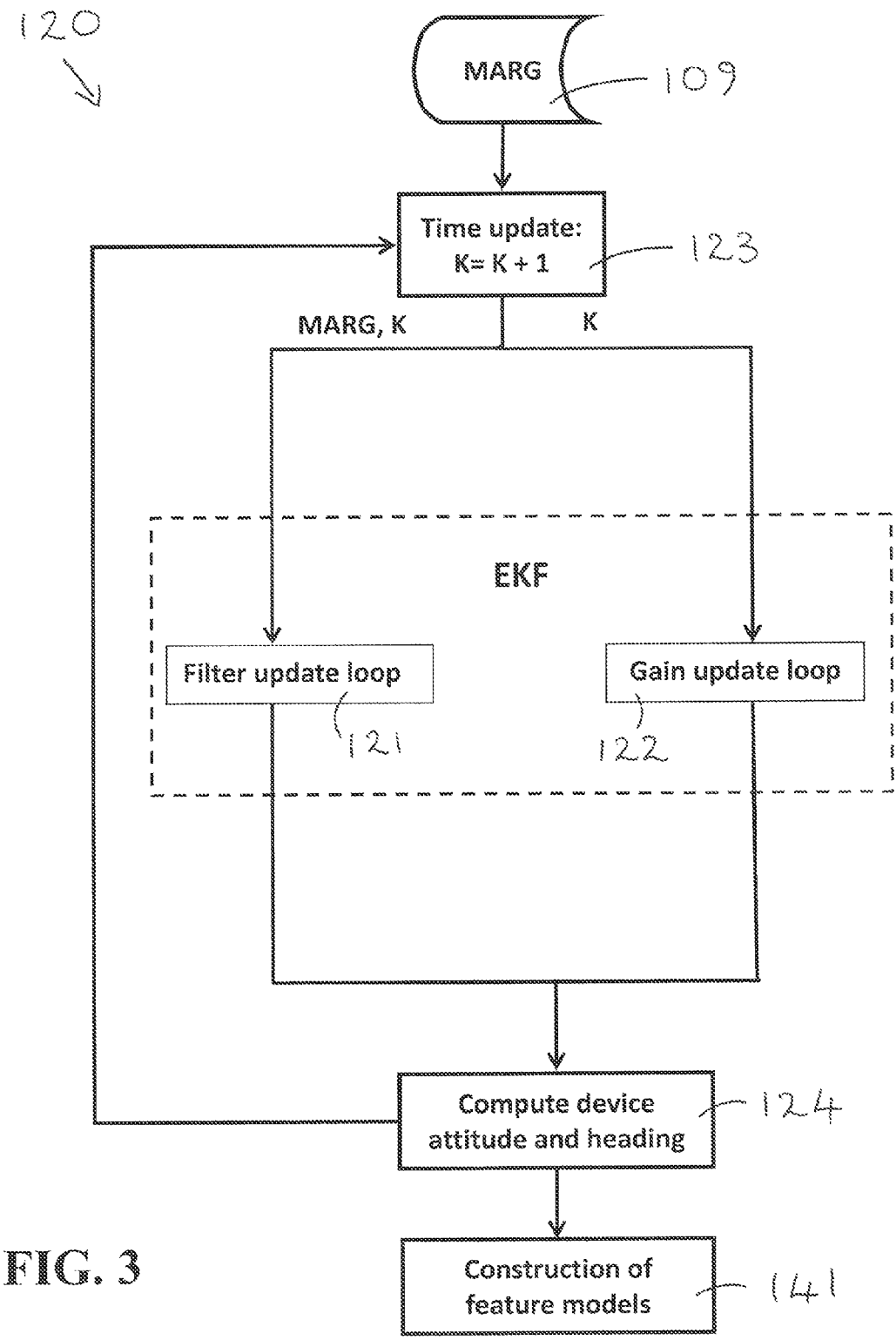
FIG. 3 depicts a detail of the EKF attitude filter of the system of FIG. 1, according to one embodiment.

FIG. 1 shows an IHM system block diagram, according to one embodiment. FIGS. 2 & 3 provide details of parts of the system. For purposes of illustration, a low-power handheld ARM-processor sensor platform device developed by Yotta Navigation is detailed herein. (An ARM processor is one of a family of CPUs based on the RISC (reduced instruction set computer) architecture developed by Advanced RISC Machines (ARM).)

FIG. 1. provides a high level generalization of the IHM system architecture. In FIG. 1, the IHM system block diagram 10 comprises platform sensors 100, comprising one or more sensor inputs such as time 101, audio 102, humidity 103, GPS 104, cellular signal 105, WiFi signal 106, Bluetooth signal 107, Near Field Communication (NFC) signal 108, Magnetometer-Accelerometer-Rate-Gyroscope (MARG) signal 109, temperature 110, altimeter signal 111, light 112, proximity sensor signal 113, and other sensor inputs 114. The platform sensors are connected to an attitude filter 120 and an IHM Event Classification unit 140. An IHM model database 130—a memory device storing IHM models—is connected to the IHM Event Classification unit. Unit 140 is connected to one or more further systems which use the classified IHM data as an input for different applications—these systems may include IHM Enhanced Navigation unit 151, Fitness unit 152, Health Monitoring Unit 153, Health Rehabilitation unit 154 and Situation Awareness Monitoring unit 155, for example.

In FIG. 2, further details of a particular embodiment of the IHM Classification System 140 and IHM Enhanced Navigation System 151 are provided. Unit 140 is shown to comprise attitude filter 120 (which may also be a stand-alone unit as shown in FIG. 1) which is connected to Feature Construction unit 141, which in turn is connected to Processing Strategy unit 142, which in turn is connected to Factorial Hidden Markov Model (FHMM) Evaluation unit 143. Unit 140 is shown configured for training, in which case output from the processing strategy unit 142 is passed to Training unit 144, which in turn is connected to IHM Event Database 145. At uniform time intervals, sensor data from Unit 100 is passed to Unit 120 where platform attitude for the time interval is calculated. The sensor data and platform attitude data is then forwarded to Unit 141. Unit 141 mathematically convolves the sensor and platform attitude data into a feature vector for each registered IHM model according to instructions contained within Unit 145. At each time interval Unit 141 forwards N feature vectors to Unit 142 where N represents the number of active registered models in Unit 145. Unit 142 then aggregates each of the N feature vectors into time ordered bundles called frames, where each frame contains P samples of a particular feature vector. When frames satisfy predetermined model specific conditions defined in Unit 145, they are independently passed into Unit 143 for classification. Upon receiving frames from Unit 142, Unit 143 evaluates the probability that the frame resulted from an instance of the registered motion, called an event, using a Hidden Markov Model (HMM) or a Factorial Hidden Markov Model (FHMM). If Unit 143 determines a statistical likelihood of an event, an event structure containing the event model name, event parameters and time is passed into Unit 151 for processing. For model training, refinement and unsupervised learning, Unit 144 aggregates frames and performs periodic updates to Unit 145.

In more detail, feature construction is performed in Unit 141 by assembling attitude and sensor from data passed from Unit 120. At each sensor time update, a feature vector is calculated for each active IHM model based upon the IHM model construction designation—see the channels specified for each model in the Table of FIGS. 5A-D, which channels are the feature constructions that comprise the feature vector. Each vector is then pushed onto a model specific circular vector buffer maintained by Unit 141. The buffer constitutes a temporal history of feature vectors (feature frame) for each motion model. The time duration (or depth) of each frame is specific to each model. Unit 141 then passes the feature frame references to Unit 142. Unit 142 performs an analysis on each frame, based upon motion model trigger requirements, to determine when and if to send the frame on to Unit 143 for motion classification. Possible trigger scenarios include time periodic frame forwarding or conditional frame forwarding based on vector component extremums within the frame.

When Unit 142 forwards one or more frames to Unit 143 for analysis, the entire feature frames are evaluated against the IHM Markov model to produce a Log Likelihood (LL) for each model. LL results are then compared to model training statistics to calculate a raw probability of an event match. If more than one model is forwarded to Unit 143 during a given time segment, a Bayesian renormalization is performed on the raw probabilities to provide a more accurate probability accounting for each motion model. When a motion model probability exceeds a specific predefined model threshold, a motion event tag containing time, statistical parameters extracted from the feature frame, and motion model ID and class are passed to Unit 152 for navigation update. The motion event tag time and statistical parameters (such as mean and variance) are used to provide a relative degree of effort associated with each motion event. In the case of locomotion, these parameters are used to estimate stride length.

Unit 145 provides Unit 141 with the list of active feature vector construction templates which may be used to calculate registered model feature vectors, and processing strategy data later passed to Unit 142. Unit 145 provides Unit 143 with IHM Markov parameters used to compute LL for each model, and provides training data statistics used to calculate raw event probabilities.

Unit 151 is shown to comprise IHM Event Processing Unit 152 which is connected to both the Navigation Update unit 153 and the IHM Dead Reckoning Database 155. Unit 151 further comprises GPS Event Processing unit 154 which is connected at an input to Platform Sensors 100 for supply of GPS data and at an output to unit 155; unit 155 is in turn connected at an output to the Navigation Update unit 153.

Unit 152 receives unqualified events from Unit 143. In Unit 152, the unqualified events are placed within a holding queue and held for a model specific timeout period. During any given time segment, if multiple unqualified events are within the queue, a Bayesian normalization of event probability is performed. At event queue timeout, if the event exceeds a model specific predetermined threshold, the event is qualified. Qualified events are then forwarded to Unit 155 for logging and storage, and Unit 153 for Navigation update. Upon receiving qualified event data from Unit 152 and user profile parameters from Unit 155, Unit 153 calculates a relative navigation update with errors. When Unit 154 receives a GPS positional update, the navigation solution is updated using GPS position and GPS positional errors. Following GPS processing in Unit 154, user profile parameters in Unit 155 are modified to reflect changes in IHM distance and relative heading parameters.

Sensor devices identified in Unit 100 are typically hardware components interfaced to the central processor where IHM computations are to be performed. Sensor data may be aggregated within a firmware layer such as a field programmable gate array (FPGA) or an application-specific integrated circuit (ASIC) to group and ensure high quality simultaneous sensor data acquisition, but is typically implemented in software within a kernel level module or real-time operating system (RTOS) level driver. Computations performed by Units 120, 140 and 151-155 are performed in software. Other embodiments may have these processes moved into FPGA or ASICs as a performance and power improving measure. In order to maintain database persistence across power cycling, data comprising Unit 130 exists on a non-volatile storage medium such as flash or magnetic media, but may be cached into fast resident memory during program operation to maximize computational performance.

Processing Units 120, 140, and 151-155 may be instantiated within a single programmatic flow or as separate kernel processes, tasks or RTOS threads across single core or symmetric multi-processing (SMP) core processing environments. In data center environments, Units 120, 140 and 151-155 may optionally be dispersed or parallel processed among different processing servers using a variety of available interprocess communication (IPC) and networking methods for communication.

At the heart of the sensor platform (100) sits a 9 axis MARG Inertial Measurement Unit (IMU). The MARG IMU is sample time synchronized and provides 16 bit sample data at a data rate of 40 samples per second per axis. The IMU data is queued into an FPGA hardware receive first-in first-out (FIFO) buffer which is then received and re-queued by the ARM central processing unit (CPU) at 200 ms intervals within a system level interrupt service routine (ISR) into an internal memory IMU FIFO buffer. (Note that the FPGA is only one possible means of sensor data aggregation used with the sensor platform.) Altimeter data may also be collected and integrated into the FPGA core state machine and included in the FPGA hardware receive buffer.

The IMU is a MARG system providing 3 axis of acceleration, 3 axis of rate gyro, and 3 axis of magnetometer measurements at a rate of 40 samples per second per sensor. Note: a rate gyro is a type of gyroscope, which rather than indicating direction, indicates the rate of change of angle with time.

FIG. 3 shows a detail of the EKF attitude filter of the system of FIG. 1, according to one embodiment. An EKE filter is used to generate IMU strapdown attitude data using IMU accelerometer, gyro and magnetometer data. Attitude data includes EKF states, yaw, pitch, and roll at each IMU sensor sample time. FIG. 3 shows the EKF 120 comprising a filter update loop 121 a gain update loop 122, a time update unit 123 and a computing unit 124. The EKF receives sensor data from the MARG 109, time stamped by the time update unit 123, and after filtering the data, device heading and attitude are computed by unit 124. The device attitude and heading data are sent to feature model construction unit 141, for construction of feature models as described below.

Figure 4:
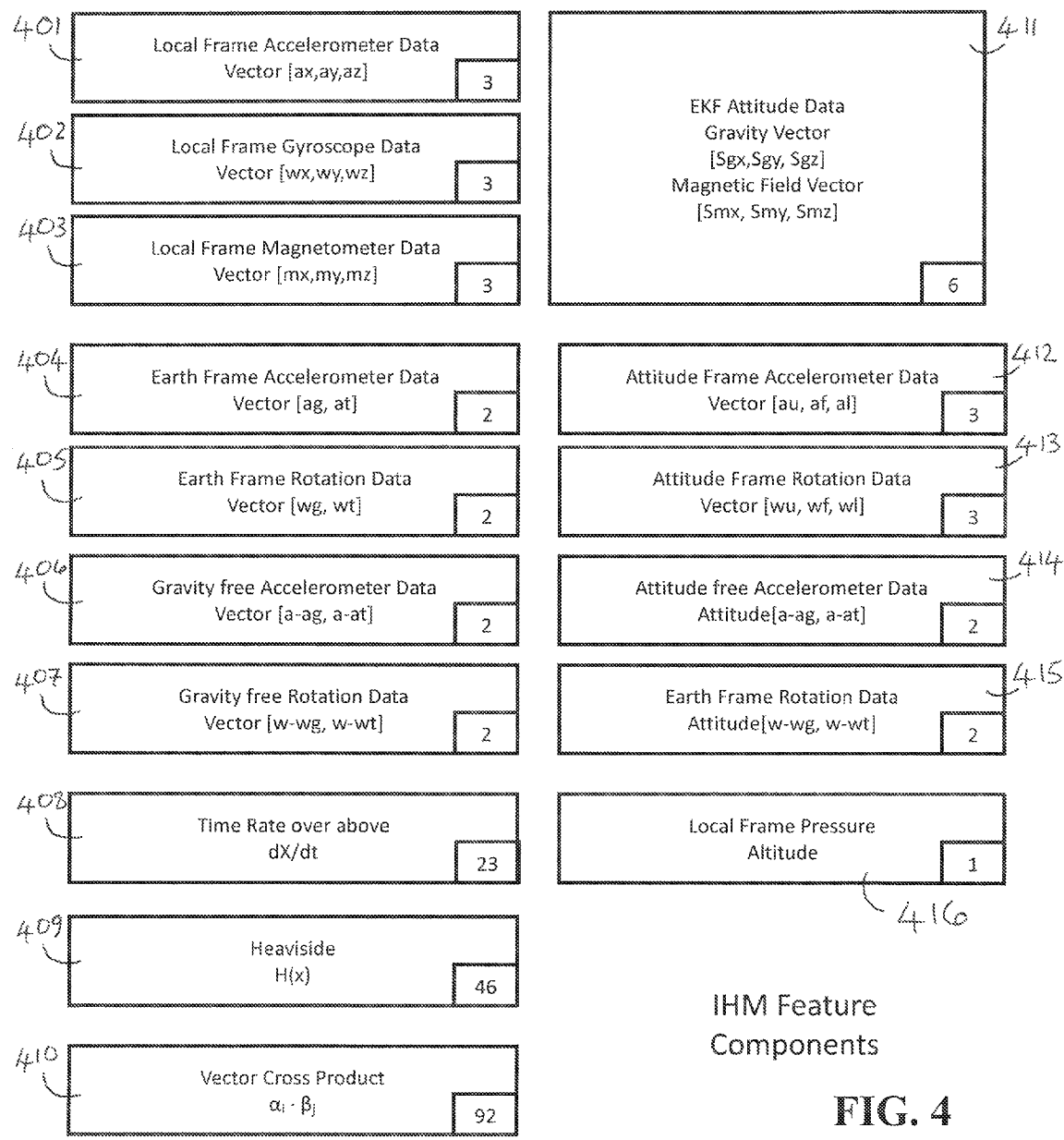
FIG. 4 depicts IHM feature components, according to one embodiment.

IHM feature components are generated by the system, as detailed in FIG. 4. (Note the number in the box in the low right corner for each group of components is the number of components in that group.) Examples of IHM Features are shown in FIG. 4; these examples include Local Frame Accelerometer Data Vector $[a_x, a_y, a_z]$ 401, Local Frame Gyroscope Data Vector $[\omega_x, \omega_y, \omega_z]$ 402, Local Frame Magnetometer Data Vector $[m_x, m_y, m_z]$ 403, Earth Frame Accelerometer Data vector $[a_g, a_t]$ 404, Earth Frame Rotation Data Vector $[\omega_g, \omega_t]$ 405, Gravity Free Accelerometer Data Vector $[a-a_g, a-a_t]$ 406, Gravity Free Rotation Data vector $[\omega-\omega_g, \omega-\omega_t]$ 407, Time Rate dX/dt 408, where X represents the above features, Heaviside Function H(x) 409, where x is dX/dt, component product $\alpha_i \cdot \beta_j$ 410, where $\alpha_i$ and $\beta_j$ are vector components of different features x, EKF Attitude Data Gravity Vector $[Sg_x, Sg_y, Sg_z]$ and Magnetic Field Vector $[Sm_x, Sm_y, Sm_z]$ 411, Attitude Frame Accelerometer Data Vector $[a_u, a_f, a_l]$ 412, Attitude Frame Rotation Data Vector $[\omega_u, \omega_f, \omega_l]$ 413, Attitude Frame Accelerometer Data Vector $[a-a_g, a-a_t]$ 414, Earth Frame Rotation Data Attitude $[\omega-\omega_g, \omega-\omega_t]$ 415, and Barometric Altitude Data (also referred to as adjusted pressure altitude) dP 416.

Feature constructions used to identify complex human motions, such as specified in FIGS. 5A-5D, are utilized to identify human motions, which may, in embodiments, then be used for dead reckoning navigation solutions as detailed herein. Note that the models indicated with an "*" are sensor platform orientation independent models, and models indicated with an "+" are sensor platform attitude independent, but body attitude dependent models. The body attitude may be identified when walking is first detected by the system, for example. Furthermore, note that in the models, the notation [1][2] represents the multiplicative product of column entries 1 and 2.

FIGS. 5A-D catalogs 38 algorithmic feature construction vector templates used in the classification of different types of motion. The model numbers refer to chronological constructions used when evaluating a model's classification efficacy. The columns are channels comprising vector components. The most simple constructions, m0, m2 and m6, are vectors whose components reflect the raw local accelerometer sensor data (A), local gyro sensor data ($\omega$), and accelerometer and gyro sensor data, respectively. Other models, such as m1 and m3, incorporate total accelerometer or gyro magnitude as a scalar. In most instances, one can ascertain that particular vector components can be expressed in terms of physically realizable quantities such as forces or angular rotations perpendicular and parallel to gravity. In other instances the vector components may not correspond to such notions, only beneficial in that the Markov Model was able to identify a non-intuitive correlation resulting in strong classification accuracy.

In further embodiments, the system may be based on a smartphone platform, such as an Android Smartphone, for which data rates are at 50 samples per second per sensor or higher, although computational performance and battery life on the Android platform may be limiting.

IHM models have been developed for a wide range of human motions, including the following: Forward Walking (WF; m27); Crawling Low (LC; m34, m37); Backward Walking (WB; m22, m23, m27, m30, m36); Crawling High (HC; m34, m37); Side Stepping Left (SSL; m35); Squatting (SQ; m27, m29); Side Stepping Right (SSR; m35); Kneeling (KN; m27, m29); Walking Upstairs (WUP; m38); Standing Up (SUP; m27); Walking Downstairs (WDN; m38); Sitting Down (SDN; m27); Jogging (JOG; m27); Running (RUN; m27); Lateral Rolling Left (LRL; m26, m32); Sprinting (SPR; m27); Lateral Rolling Right (LRR; m26, m32); Running Jump (JMP; m29); Forward Rolling (FR; m26, m33); Backward Rolling (BR; m26, m33); Standing Long Jump (SLJ; m10, m22, m27, m29); Spinning Clockwise (SPNC; m26); Spinning Anti-clockwise (SPNA; m26); Standing (Fidgeting) (FIG; m7, m27); Stair stepping Up (SSU; m27, m38), Stair stepping down (SSD; m27, m38); and General Concussion (GC; m27, m31). The model numbers (m#) refer to those of FIGS. 5A-5D.

An IHM Suite (IHMS) has been used to help facilitate the analysis and training of IHM models. The IHMS in some embodiments is composed of four parts: software programming API, UNIX command line interface (CLI) utilities, a collection of scripts to facilitate job processing, and a database of IMU sensor data of human motion. The software programming API allows users to integrate IHMS routines to optimize Markov model parameters, evaluate likelihood of human motion matches, and provide parametric effort levels associated with model matches within their own code segments. UNIX command line utilities, on the other hand, can be used as a standalone means to generate, optimize and evaluate the human motion models, specifically those residing in the Human Motion Database (HMB). BASH (Bourne Again Shell) scripts have been provided to coordinate and simplify bulk processing automation of the HMB. The HMB is a large collection of streaming inertial and sensor data categorized into over 20 different anthropocentric human motion activities.

The IHMS API consists of library function calls divided into the three categories: IMU data preparation and feature construction; Factorial Hidden Markov Model (FHMM) optimization and model analysis, and diagnostic and debug support. Data preparation routines allow the user to calibrate, filter and generate streaming feature models from streaming IMU and other sensors. Then FHMM models are generated and optimized based on a number of parametric considerations including state size, independent chains, transition probability restrictions and frame size using FHMM optimization routines. Following optimization, the strength of the models may be tested using analysis against other data sets to insure strong motion class resolvability and reliability. Once completed, models may be exported into ASCII readable files for import onto mobile and handheld devices. Diagnostic and debugging support APIs permit intermediary dumps of proprietary data structures into CSV files easily readable within analysis packages such as Microsoft® Excel, MATLAB®, Mathematica, Maple, GNU Octave and LabVIEW™ and Scilab.

In a typical training scenario, raw IMU data of given human motions are collected using the sensor platform device and stored onto a removable Micro SD Flash drive or other non-volatile memory. Once a sufficient volume of data is collected, it is transferred to a Linux based PC workstation either by physically removing the sensor platform MicroSD flash and placing it into the workstation multimedia port or by transmitting the data over the USB or a wireless connection. The IMU data is then processed using the IHM utilities and a classification model parameters file is generated. The resulting model parameters are lastly transferred back to the sensor platform and used for IHM classification and navigation dead reckoning.

The sensor platform is then firmly attached to the subject at a fixed location and the human motion activity can commence. Care should be taken to avoid mounting positions where the sensor platform may bounce or twist independent of the subject. For instance, placement in a loosely fitted pouch provides a less consistent IHM signal than when strapped firmly against the subject. The position of the sensor package on the subject may be varied, although when worn in a fanny pack it has been found to be advantageous particularly when utilizing the IHM data for navigation reconstruction.

Figure 6:
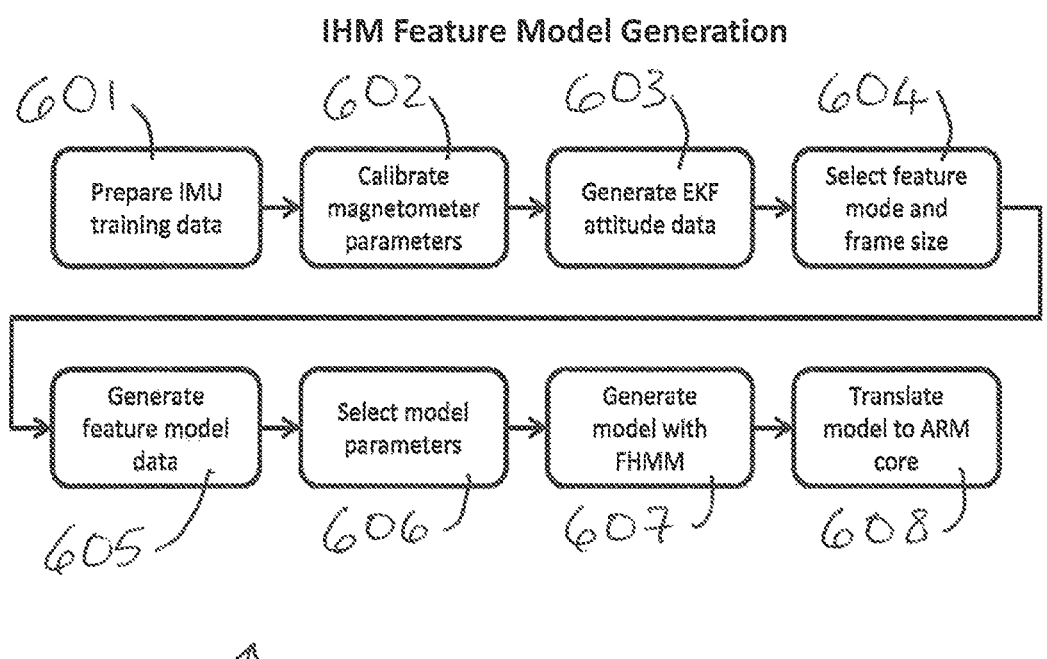
FIG. 6 depicts a flow diagram for generation of an IHM feature model, according to one embodiment.

IHM feature construction in some embodiments is illustrated by the flow 60 in FIG. 6, which consists of the following process: prepare IMU data (601); calibrate magnetometer parameters (602); generate EKF attitude data (603); select feature mode and frame size (604); generate feature model data (605); select model parameters (606); generate model with FHMM (607); and translate model to ARM core (608).

The flow 60 is described in more detail as follows. Once human motion training data has been collected and moved to the Linux based PC, the data is processed into a loadable IHM model for use on the sensor platform using a series of command line utilities. Among these are bcal for determining magnetic field calibration parameters, ekf for generating an attitude heading reference, and fmlex for generating the model feature data.

The bcal utility is used to generate magnetic field parameters for the device and/or data set if calibration parameters have not been previously determined. It is not necessary to determine the magnetic sensor calibration parameters if the sensor platform magnetic field calibration parameters have already been determined at a time prior. However, periodic recalibration of the parameters may need to be performed to insure hard and soft core hysteresis in the sensors does not drift substantially over periods of time. Using an incorrect set of magnetic sensor calibration parameters will generally not impact IHM classification by a great deal, but it will result in attitude heading deviations during the dead reckoning navigation reconstruction modules.

Once magnetic sensors have been calibrated, the next step is to run the raw IMU sensor data through an Extended Kalman filter (EKF) attitude filter using the ekf utility. The EKF attitude filter is responsible for filtering device attitude pitch, roll and yaw from external acceleration forces. The resulting data file consists of the EKF filter state vectors and angular measures for roll, pitch and yaw. The yaw direction is currently determined relative to the body frame heading axis.

Next, the feature construction step is when the user must make decisions regarding composition parameters of the IHM model construction. The first decision is deciding on feature model construction. For example, thirty-six model construction types labeled m0-m38 (m17 and m18 being deprecated) are shown in FIGS. 5A-5D, and also provided in the program listing at the end of the detailed description. In general, a single feature construction type does not perform optimally with different human motion activities, so it is important to explore what feature construction works best for each human motion model targeted.

Along with the feature construction type, a frame size must be selected. A frame size is relative to the approximate duration of the repetitiveness of the human motion being modeled. At the sensor platform sample rate of 40 Hz, a frame size of 80 samples translates to approximately 2 seconds. It is important that the frame size is large enough to encompass one iteration of the human motion activity. Typically a fast walking pace can have an iteration time as small as 1 second, and over 2 seconds for a slow pace for an average person. Assuming a 40 Hz sample rate, this corresponds to a frame size of 40 to 80 samples. This is similar for walking backwards. Jogging, on the other hand, has an iteration time ranging from $\frac{1}{2}$ second (20 samples @ 40 Hz) to around 1 second (40 samples @ 40 Hz), and Running has an iteration time of less than $\frac{1}{2}$ second (20 samples @ 40 Hz). If the frame size is set too small, only a portion of the motion activity will be trained. If the frame size is too large, the IHM model will be trained to identify multiple cycles of the activity and will potentially fail to identify a single instance of the motion. Each different human motion activity may have a different frame. Walking forwards may have a frame size of 80 for instance, while running jumping performs better with a frame size of 40. Further examples of Frame Size Ranges are provided in Table 1; note that the optimal ranges are examples of an optimal range for some embodiments. Once the feature model and frame size are selected, feature model data is generated from the IMU and EKF attitude data using the fmlex (feature model lexical construction) utility.

The next stage is to determine the number of states and model chains to be used in the IHM FHMM. Optimally, the number of states should be equal to the frame size. Anything larger cannot improve IHM classification performance but adds greatly to computational demands. The larger the number of states, the better the classification engine can determine the motion performed, but at a higher computational cost. On the other hand, if the number of model states selected is too small, the classifier will have difficulty identifying the human motion activity from random noise or fidgeting. Complex human motions require a larger number of states while more simple motions require less. It has been observed by the present inventors that a good number with which to start is approximately slightly greater than $\frac{1}{4}$ the frame size.

FHMM differ from HMM in that they permit multiple independent chains of states to account for multiple independent processes within the model data. Selecting the model to contain only one chain results in an HMM, while multiple chains are regarded as FHMM. Because computational demands for FHMMs increase factorially with the number of chains, in some embodiments the number of chains is kept as small as possible. In some embodiments it is recommended one starts by defining one chain (HMM), and move on to more chains if classification accuracy is not sufficient. Lastly, one must choose the topology as Ergodic or N-Bakis. The Ergodic models are computationally the heaviest and are not recommended for real-time implementation on the sensor platform device. It is recommended however that the Ergodic model is run first. An examination of the Ergodic model transition probabilities can generally determine how closely neighboring states are connected within the model data. Then an N-Bakis model may be made where N forcibly restricts state transitions resulting in a substantially lighter model with the same classification accuracy. Once the state size, chain count and model topology have been determined, the model parameters can be generated using the fhmm utility.

Figure 7:
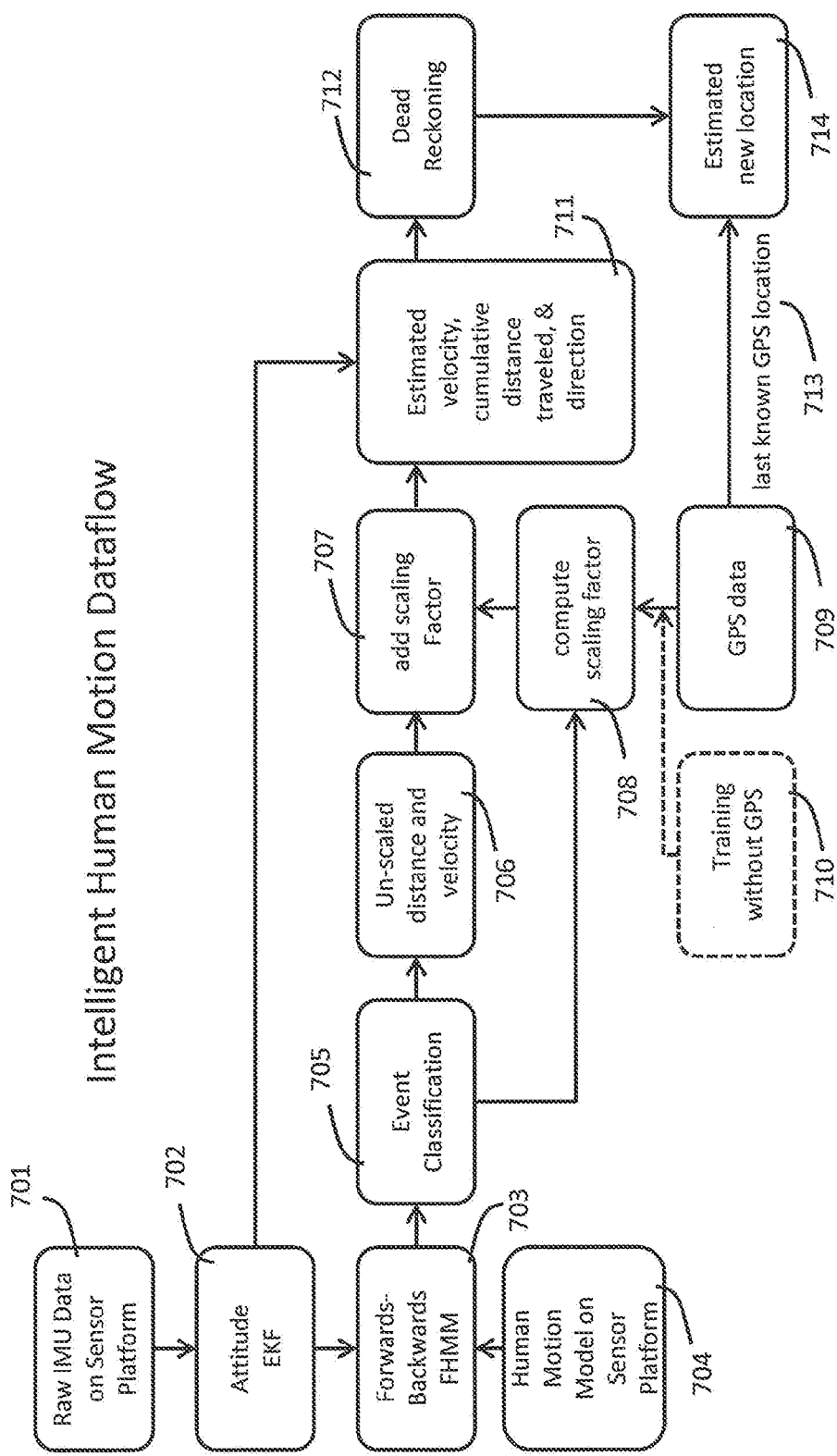
FIG. 7 depicts a flow diagram for use of IHM data for dead reckoning, according to one embodiment.

Once the IHM models have been installed human motion can be detected, classified and used to enhance dead reckoning navigation (for use in GPS denied environments), as illustrated in FIG. 7 for an example of the particular case of detecting forwards or backwards walking, for example. The process flow starts with generation of raw IMU data on the sensor platform (701), which is then used to generate EKF attitude data (702). The attitude data from (702) is processed according to the forwards-backwards FHMM (703) using the motion model parameters saved in memory (704). These parameters include but are not limited to the feature construction, smoothing filter size, window size, frame size, state transition matrix, and prior vector for each motion model. The forwards-backwards algorithm outputs a log

TABLE 1

IHM Frame Ranges

| Motion Name | Time Range for a Single Iteration (sec) | Optimal Time Range for a Single Iteration (sec) | Sample Rate Range(Hz) | Typical Frame Size (samples) |
| --- | --- | --- | --- | --- |
| Walking Forwards | 1-3 | 1-2 | 30-80 | 80 |
| Walking Backwards | $\frac{1}{2}$-2 | 1-2 | 30-80 | 80 |
| Jogging | $\frac{1}{4}$-1 | $\frac{1}{2}$-1 | 50-80 | 40 |
| Running | 0-$\frac{1}{2}$ | 0-$\frac{1}{2}$ | 50-100 | 40 |
| Jumping | 0-1 | 0-1 | 30-80 | 10 |
| Crawling | 1-4 | 1-4 | 30-50 | 80 |
| Lateral Roll | $\frac{1}{2}$-1 | $\frac{1}{2}$-1 | 30-80 | 40 |
| Forward Roll | $\frac{1}{2}$-1 | $\frac{1}{2}$-1 | 30-80 | 40 |
| Backward Roll | $\frac{1}{2}$-1 | $\frac{1}{2}$-1 | 30-80 | 40 |
| Stair Stepping (Up) | $\frac{1}{2}$-3 | $\frac{1}{2}$-3 | 40-80 | 80 |
| Stair Stepping (Down) | $\frac{1}{2}$-3 | $\frac{1}{2}$-3 | 40-80 | 80 |
| Sitting down | $\frac{1}{2}$-1 | $\frac{1}{2}$-1 | 40-100 | 50 |
| Standing up | $\frac{1}{2}$-1 | $\frac{1}{2}$-1 | 40-100 | 50 |
| Concussion | 0-$\frac{1}{2}$ | 0-$\frac{1}{2}$ | 100-2k | 100 | likelihood estimation for each model which is passed to event classification (705). The event classification evaluates all log likelihoods and determines the single most probable motion event, if any, based on how close each log likelihood matches the expected log likelihood for that event model. If a motion is detected an unsealed distance and velocity is computed using the EKF attitude state and an un-scaled distance measurement that is associated with each model during model construction (706). A scaling factor is then applied to the un-scaled value (707). When GPS data (709) is available, the scaling factor for each motion is computed periodically using an automated calibration routine (708). The calibration is computed when two conditions are met: first that the position has changed by a substantial amount according to GPS measurements and secondly that a majority or greater of the motions detected during the change in position are of the same motion. If GPS is unavailable the scaling factor may be approximated by directly evaluating the raw IMU and attitude EKF data (710). The velocity, cumulative distance traveled, and direction of travel is then computed (711). The last known position is updated by adding to it the newly computed distance traveled in a direction based on the estimated heading. This is called the dead reckoning position (712). When GPS is available (709), the new location estimation is the combined average of the dead reckoning position (712) and GPS position (713) weighted by the known error of the GPS position and the estimated error of the dead reckoning position (714).

Figure 8:
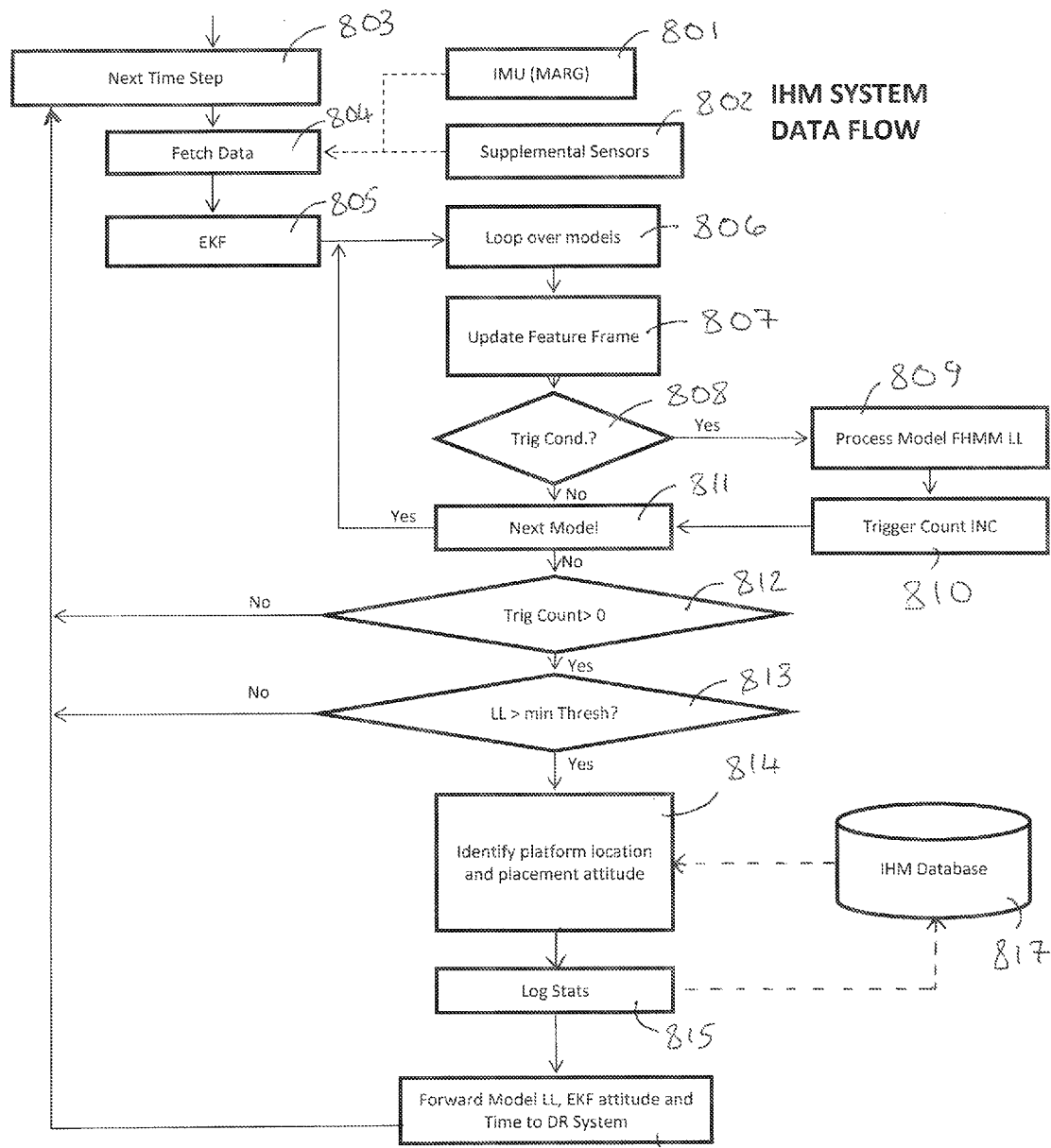
FIG. 8 depicts a flow diagram 80 showing operation of an IHM system, according to one embodiment.

A more detailed data flow showing the operation of the IHM system is provided in FIG. 8. For each time step 803, sensor data is pulled from the IMU 801 and supplemental sensors 802 by the fetch data command 804, the sensor data is aggregated and then passed on to the EKF 805. The EKF 805 inserts platform attitude into the data and passes the data along to 806 to loop through 806-811 for each active model. For each time slice and active model in 817, a numerical feature vector is calculated and temporarily stored in 807. If the number of stored feature vectors for a model exceeds a predefined threshold specified in 817, the oldest model feature vector is deleted. When a model collection of stored feature vectors satisfy model feature conditions specified in 817, the trigger condition for 808, the collection of model feature vectors are forwarded to 809 for FHMM model evaluation, and the trigger count in 810 is incremented. 811 and 806 repeats the process for each active model. If all models have been processed, 811 passes control to 812. If one or more FHMM model evaluations of 809 are indicated in 810, a list of results from 809 is passed to 813, otherwise control is passed back to 804. 813 accepts data from 809 and computes motion event probabilities. If any motion probability exceeds the model likelihood threshold, all related motion data is passed to 814. Otherwise 810 trigger is reset and processing resumes at 804. 814 processes the model and motion data to estimate and update the physical location and relative attitude of the sensor platform on the subject, and constructs an event tag. Event tag statistics are managed in 815 and stored in 817. Event tags are then made available to registered applications via an IHMS service. The IHMS allows any number of other programs operating on a platform or within a network to subscribe to the service and request delivery of real-time IHM event tag updates. Finally, in 816 model log likelihood, EKF attitude and time may be forwarded to a dead reckoning system, before the process is repeated for the next time step.

Figure 9:
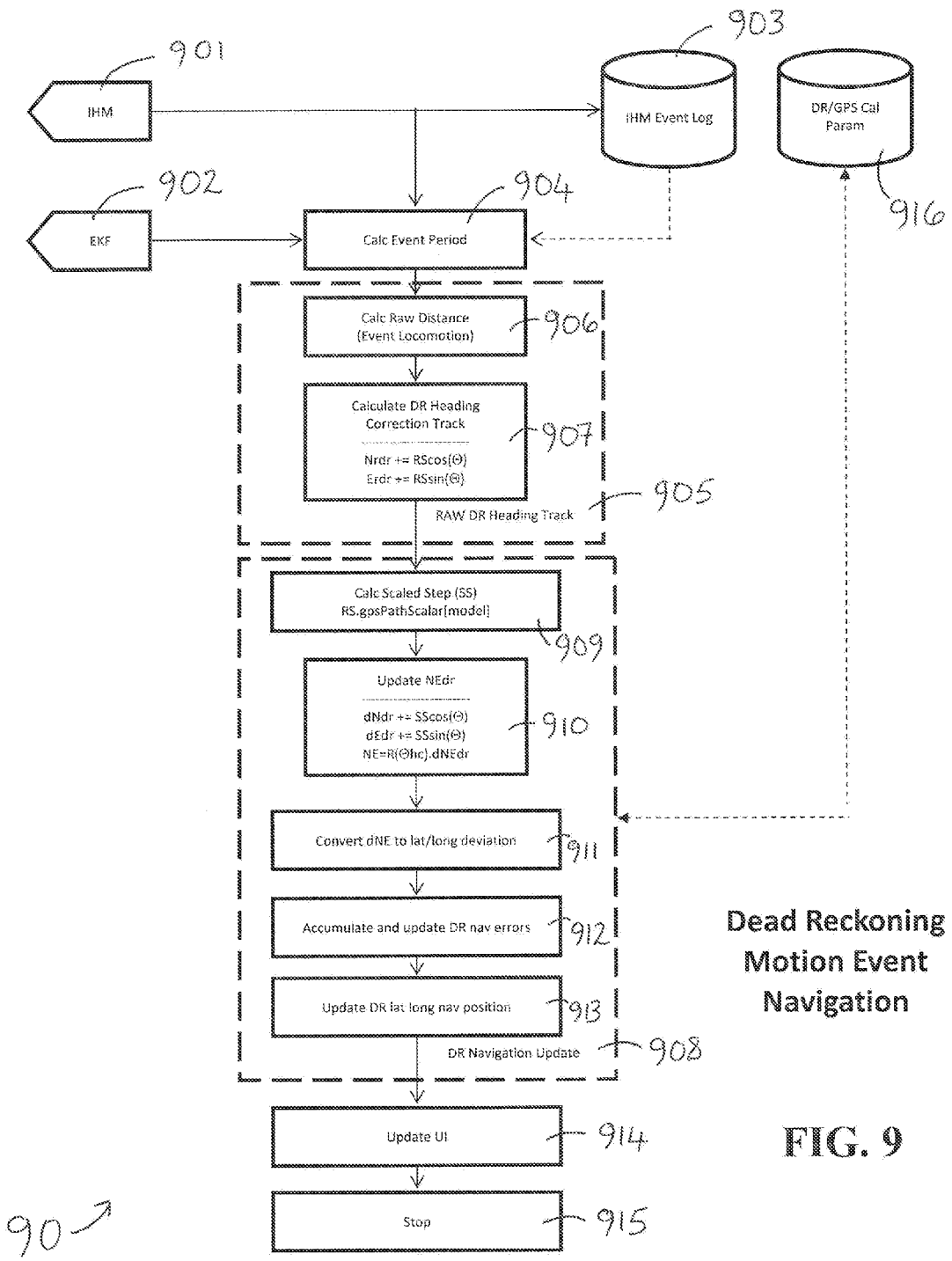
FIG. 9 depicts a flow diagram 90 showing dead reckoning motion event navigation using IHM, according to one embodiment.

FIG. 9 illustrates the processes by which IHM events are used to update a change in navigation solution according to some embodiments. The processes rely on bearing corrections and distance scalars calculated in the GPS event driven processes in FIGS. 10A & 10B.

In FIG. 9, Unit 904 receives IHM event tag information from IHM system 901 and IHM event log 903 and EKF platform attitude data from EKF 902. On each IHM event, Tag information including IHM event class, name, time of the event and other inertial sensor data statistics within the event frame are received by Unit 904. This information is then passed on to Raw DR Heading Track Unit 905. Event periodicity (time between successive matching events) is then combined with frame inertial sensor data statistics in order to calculate an empirical formula based raw locomotion distance in Unit 906. Unit 907 uses the raw locomotion distance along with a model specific platform attitude bearing to create a model specific locomotion displacement vector. The displacement vector is then added to a vector accumulator—see Unit 1021 in FIG. 10B.

Figure 10A:
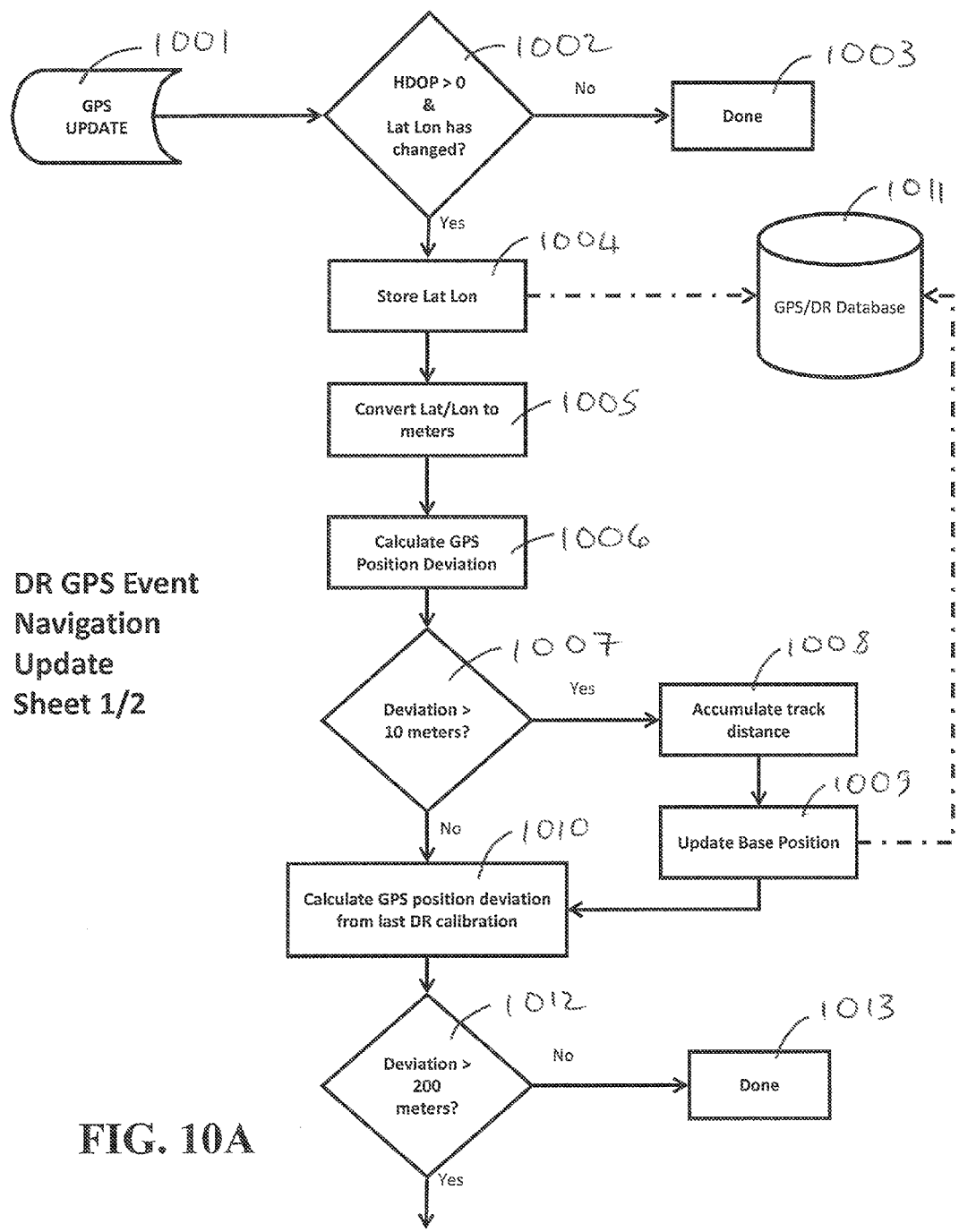
FIGS. 10A & 10B depict a flow diagram showing dead reckoning GPS event navigation updates, according to one embodiment.

Processing continues in DR Navigation Update Unit 908. An estimated true distance traveled per event is found in Unit 909 simply by multiplying the raw locomotion distance by the model specific GPS path scalar (calculated in Unit 1021). Unit 910 then calculates an IHM event driven navigation update in terms of North and East using the estimated distance traveled and event bearing offset (both calculated in Unit 1021). Finally, unit 911 converts the North and East update into traditional longitude and latitude using dLat/dN and dLong/dE—the latter are calculated in Unit 1005 (FIG. 10A). Unit 912 is responsible for accumulating IHM navigation errors, and Unit 913 adjusts the final navigation latitude and longitude to minimized GPS and IHM solution errors. Unit 914 provides the revised navigation solution to the user interface and the process stops at 915. The process is repeated for each IHM motion detected.

Figure 10B:
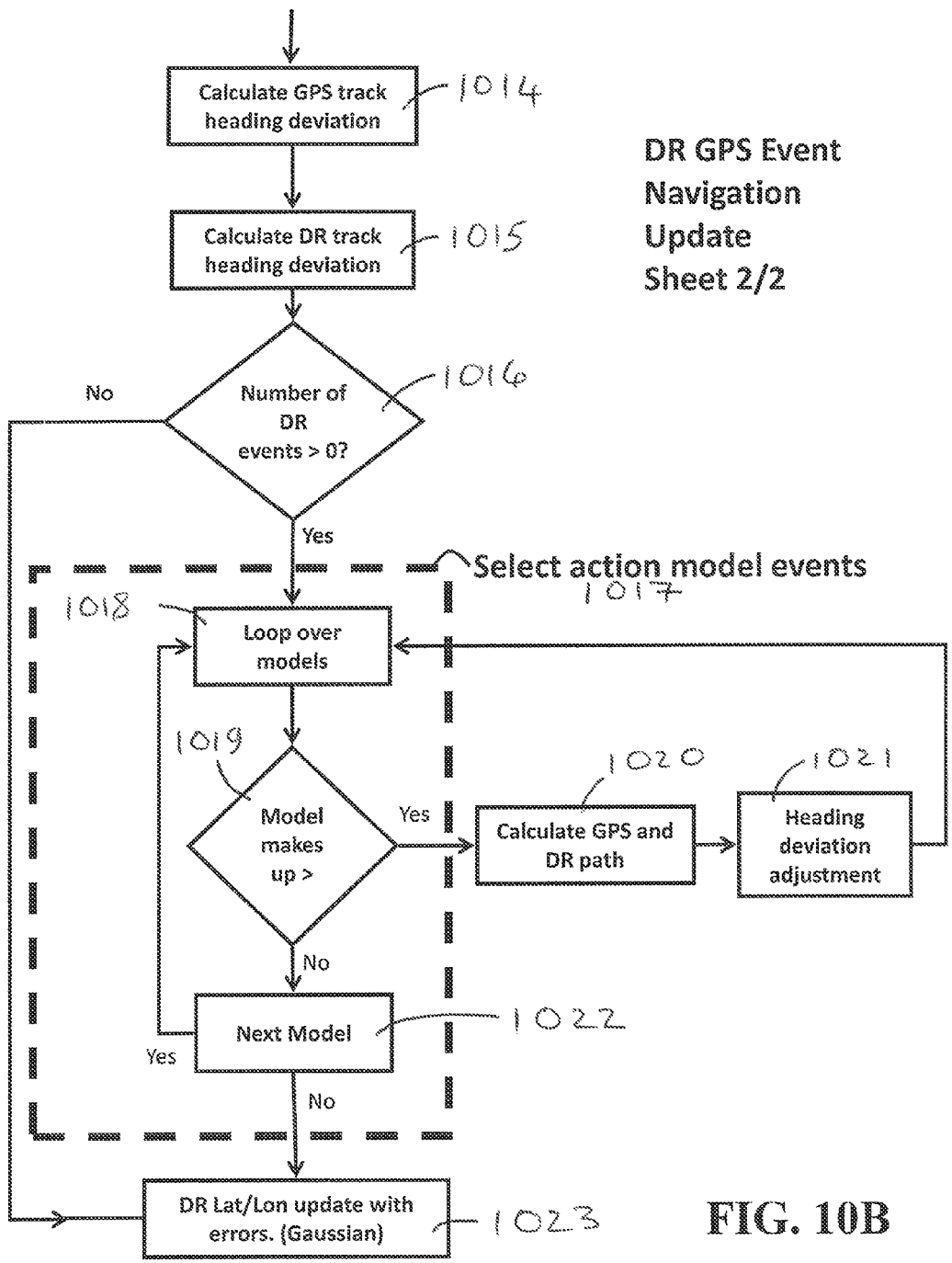

FIGS. 10A and 10B illustrate the processes by which GPS ranging data received from a GPS receiver is processed and used with IHM DR (dead reckoning) enhanced navigation, according to some embodiments.

In FIGS. 10A and 10B, a GPS ranging signal is received by the GPS system providing time, latitude, longitude, number of ranging satellites used in the navigation solution, and a factor corresponding to GPS positional accuracy (commonly given as Horizontal Dilution Of Precision (HDOP), Circular Error Probability (CEP), Elliptical Error Probability (EEP), Distance Root Mean Squared (DRMS), Radius Of 95% (R95), etc.)—GPS Update 1001. When Unit 1002 receives a GPS update whereby the positional error is unknown or excessively large (insufficient number of satellites to form a solution, etc.), the message is logged and discarded—Unit 1003. If the GPS message contains reasonable GPS positional error (for instance, less than 30 meters), the GPS position is logged by Unit 1004 into the GPS/DR Database in Unit 1011. Unit 1005 uses the GPS position to update two scalar registers containing dLat/dN and dLong/dE where dN is meters Northing, and dE is meters Easting. Unit 1006 calculates a (dN,dE) vector change in position since the last GPS update. If the deviation exceeds a minimum threshold (typically 10-20 meters) in Unit 1007, the deviation is added to a GPS track accumulator in Unit 1008 and in Unit 1009 the base position update is logged in Unit 1011. Unit 1010 calculates the total GPS track distance traveled since the last DR calibration was performed. If the distance exceeds the calibration minimum (typically 100-500 m), Unit 1012 passes control to Unit 1014 for DR calibration. Otherwise, the data processing is complete, Unit 1013, and the process continues at Unit 1023.

Unit 1014 calculates the mean bearing traversed over the GPS track since the previous DR calibration. The mean bearing is easily found as the Arctan of the GPS track accumulator vector components. Unit 1015 calculates the total linear path distance of the GPS track since the previous DR calibration. Unit 1016 evaluates the number of different IHM motion classes associated with the GPS track. Unit 1016 may be used to ensure that changes in GPS position resulting from other than IHM motion (for instance auto locomotion) does not create errors in calibration factors, and is the gate keeper to the select action model events module 1017, which includes a loop over models implemented by units 1018, 1019 and 1022, calculating GPS and DR path (1020) and heading duration adjustment (1021) for each model. Note that since zero IHM events would result in Unit 1019 always returning false, Unit 1016 may be removed without consequence in embodiments. If the number of IHM events was non-zero and each IHM event type composed more than a threshold fraction of the total IHM events (typically 90%), Unit 1019 would result in an updated value for that particular IHM model GPS path scalar (Unit 1020) and IHM model heading deviation scalar (Unit 1021).

Unit 1023, similar to Unit 913, is responsible for combining an updated GPS and IHM DR navigation solution using both HDOP and IHM accumulated errors. Following completion of Unit 1023, the DR GPS Event Navigation Update is suspended until a new GPS ranging signal is received at Unit 1001.

Feature Model Lexical Construction

The finlex utility, fmlex <-NA>[model] [frame] [start] [stop] [filebase . . . ], is used to generate feature model lexical frames used within model training and classification. Natively, there are 39 feature models constructions identified as m0-m38. Additional feature constructions may be programmed in the form of link libraries using the fmlex.h header file.

The feature model, [model], is the arithmetic construction of the IMU sensor, attitude and other sensor data into vectors used for model optimization and classification. In FIGS. 5A-5D is a table of 38 feature constructions natively supported by the fmlex utility. Additional feature constructions may be added by compiling functions conforming to the finlex.h API into dynamic link libraries. In general, different motion classes may be constructed using different feature models.

A feature frame, [frame], is composed of a fixed number of feature model samples. Any given motion model class requires a fixed frame size making up a framing window (or frame). If the IMU sample rate is 40SPS per axis, a frame of 80 feature samples constitutes approximately 2 seconds of data. Motion classes with relatively long repetition times, such as walking, require larger framing windows, whereas shorter motion classes, such as jumping, require shorter framing windows.

The start position, [start], is the sample time at which feature encoding should begin. If zero or less is specified, the beginning of the IMU and attitude is assumed.

The stop position, [stop], is the sample time at which the feature encoding stops. If [stop]<=[start], the stop position is assumed to be the last of the IMU and attitude data. The purpose for [start] and [stop] options is to allow the user to only select pertinent data from the IMU and attitude data files. Such is the case when training data motion needs to be restricted to only one type of motion. Setting lower and upper cuts removes IMU data that may coincide with activities NOT part of the motion class.

FHMM—Factorial Hidden Markov Model Optimization

The fhmm utility, fhmm [chains] [states] [range] [eye] [tol] [filebase . . . ], is responsible for the generation of model parameters which optimize to the largest log likelihood (LL) against the training data [filebase].

The number of independent state chains, [chains], is specified as the first command line parameter. The number of independent chains (M) determines the number of independent processes for which the Markov Model attempts to fit. Each state chain will contain K states. One independent chain defines a typical Hidden Markov Model. When there is more than one chain the model is referred to as a Factorial Hidden Markov Model, and can be viewed as multiple Markov processes. The processing requirements of the Factorial model increases factorially, and the number of model parameters increases exponentially as $K^{2M}$.

The number of states, [states], in each of the state chains is specified by the second command line parameters. The number of states roughly correlates to the number of independent variables required in order to successfully fit the Markov model to the data. If the number of model states is insufficient to effectively model the fitting data, one will find that the model will have difficultly resolving the human motion class training data from other data human motion class data. If the number of states specified is larger than required, the model will easily distinguish human motion training data to that of other human motion classes. But it may have difficulty identifying model human motion data slightly deviated from the training set, such as data variances seen between different subjects. Using larger numbers of states also has the effect of greatly increasing the processing requirements of the model. Finding the correct number of states to effectively resolve human motion within motion classes across different subjects is an iterative process.

The range parameter, [range], is used to limit model state transitions between neighboring states. A range parameter of 0, 1 or greater than or equal to the total number of states disables state transition limiting, which results in an Ergodic model. An Ergodic model allows a transition between any Markov states in one transition interval. Values greater than 1 and less than the total number of states will result in a Bakis model. A Bakis model restricts state transitions to neighboring states and only in a forward direction. For instance, a range restriction of 2 only allows two possible state transitions: a state transition to itself or a state transition to the next forward neighboring state.

The cyc parameter, [cyc], specifies the maximum number of optimization iterations allowed to achieve a local maximum log likelihood. If the maximum number of iterations is reached, the fhmin utility aborts its efforts to find a solution.

The tolerance parameter, [tol], specifies the numerical tolerance used when determining whether a local maximum log likelihood optimization condition is met. If the tolerance is set too small, the fhmm will exhaust the [cyc] maximum number of optimization attempts and abort.

FHMM optimizes over all *.lex files within the HMD motion class. Model optimizations are performed over a collection of chain, state and transition range sizes. Because model optimization is numerically heavy, the build_fhmm script automatically runs 10 parallel optimization process threads at a time. Typical run times over the HMD are on the order of days.

Factorial Hidden Markov Model Forward/Backward Evaluation

The fhmm_cl utility, fhmm_cl [name] [fhmm file] [fmlex file . . . ], performs log likelihood calculations of feature data frames against a target optimized model. The utility may be used for the classification of unknown human motion feature frames against known models, the evaluation of model reliability and resolvability when used with known human motion feature data.

The analyze_fhmm script provides forward/backward model LL calculations of all HMD data against all models within the HMD. Similar to build_fhmm, because model optimization is also numerically heavy, the script automatically runs 10 parallel forward/backward processes at a time. Typical run times of analyze_fhmm are on the order of hours.

Sorting FHMM Forward/Backward Evaluation fhmm_sort_cl [fhmm file] [stddev] [outfile] [fmlex file . . . ]

The fhmm_sort_cl utility performs a fhmm forward/backward evaluation of LL of frames contained in finlex files against model parameters located in the fhmm file. The purpose of the utility is to provide a means to extract strong LL frames within an unstructured feature data and place them into a common file.

Development of the Walking IHM Feature Model

In the case of a walking forward motion feature model, although the rate of rotation around the Sg vector does provide a strong signal of the subject walking, it heavily biased the walking model only to detect walking in a straight line—it was found that when the subject walks even a large radius of curvature, the walking model would fail to detect the walking forward motion because the rotation around Sg contained a dominant linear composition of the average yaw. In order to keep the rate of rotation around the Sg axis, and yet detect the walking forwards motion, time differentiated IMU sensor data was utilized; however, differentiating the rate of rotation would only remove any constant rate of rotation when a person was walking and turning. Thus, the sign of the time derivative V(du/dt), where V(x)=2*H(x)−1 and H(x) is the Heaviside step function H(x)=+1 (x>0), 0 (x<0) was used. Furthermore, using only phase information within a model construction fails when the subject is fidgeting. So in order to allow some type of motion intensity into the model, at least one component is analog. In the case of walking (model 27), three analog channels are used: magnitude of force along gravity, magnitude of forces perpendicular to gravity, and rotations perpendicular to gravity (pitch and roll). A single analog component is also needed in order for the model to support event level triggering (based on the coding implementation of the trigger in our software). In conclusion, the walking forward model utilizes both analog and time derivative V(du/dt), where V(x)=2*H(x)−1, as detailed in model 27 below.

As can be seen from an inspection of FIGS. 5A-5D, the function V(x) is used in a number of human motion models, for example walking forwards, jogging, running, side stepping left, side stepping right and walking backwards, among others. Furthermore, it has been determined that the walking forwards model may also be readily adapted for identifying the human motions standing up and sitting down.

Note that the vectors $S_F^{walk}$, $S_L^{walk}$, $S_U^{walk}$, which are found in models 30, 32, 33, 35, 36 & 37, are defined as the respective Forward, Left and Up vector attitude directions of the sensor platform identified when walking motion events are identified; these vectors are derived from Sg. The matrix form $R^{walk}$ is defined as the equivalent matrix $R^{walk}=(S_U^{walk}, S_F^{walk}, S_U^{walk})$. These vectors provide statistical information regarding sensor platform orientation, placement location, and subject posture which are then used to enhance navigation accuracy, improve subsequent IHM classification accuracy and identify when the sensor platform has been handled and or relocated when the subject is or has been walking.

Navigation accuracy is supplemented using the vector $S_F^{walk}$ conjunction with platform magnetic data to improve navigation bearing when the subject is walking. Because many human motions are restricted to specific posture attitudes, classification accuracy and reliability of those models, for instance crawling, lateral rolling, pushups, pull-ups and jumping jacks are greatly enhanced when posture attitude data is incorporated. Crawling, lateral rolling and pushups cannot occur if the subject is not body prone to the ground. Similarly, pull-ups and jumping jacks cannot occur unless the subject is in a torso upright posture. The handling and relocation of the sensor platform on the subject is identified when the platform attitude is found to have statistically changed over two or more walking events. Because walking is among the most prevalent motions people perform each day, it is the predominant motion attitude used to supplement navigation and classification accuracy with regards to platform orientation, placement and subject posture.

Examples of IHM Feature Models

Examples of feature models are provided below. The specific IHM motion models are identified by name model parameters (as used in the Table of FIGS. 5A-5D), this example being for the Walking model:

_Walk.1234abcd-20141208-173850.m27_s1_t−2_w40 f80.M1_K25_112.T80.MOD where the name provides the following information:

Model Name: _Walk

Device serial number: 1234abcd (serial number of device which collected training data)

Date: 20141208 (UTC date when training data collection began)

UTC Time: 173850 (UTC time when training data collection began)

Model number: m27 (Feature model construction)

Sensor smoothing: s1 (Boxcar IMU smoothing parameter)

Trigger condition: t−2 (t=−2 is time framing, t>0 is event framing adjusted to value in frame)

Trigger window size: w40 (Defines time domain for identifying local trigger maximums)

Frame size: f80 (number of time samples used when training an IHM model)

Independent Markov chains: M1 (M=1 Basic HMM, M>1 Factorial HMM)

Markov States per chain: K25 (i.e., K=25 states)

State transition restrictions: R2 (R<2: Ergodic model, R>1: Bakis model restricting transition to R states)

Frame size: T80 (Markov frame size—same as f80)

Model 27, utilized in identification of walking, is as follows:

model 27: //three analog channels plus base sign diff [size 6] (WALKING MODEL)

tlex[0]=(Sg*a); //force along gravity vector twg=(sg*w); //rotation along gravity vector (heading change);

tlex[1]=(a-Sg*tlex[0]). Mag( )//forces perpendicular to gravity vector tlex[2]=(w-Sg*twg).Mag( )//rotation perpendicular to gravity vector (heading change);

//assign 3 raw channels

```
for (i=0; i<3; i++)
    lex[i]=tlex[i+3]=tlex[i];
//apply differential sign of each channel
for (i=3; i<6; i++)
{
    lex[i]=(tlex[i]>m_prev[i]?1: -1);
    m_prev[i]=tlex[i];
}
```
© 2015 Yotta Navigation Corporation Feature construction of model 38, utilized in identifying traversing stairs in an upward and downward direction is identical to model 27 but with the addition of altimeter sensor data.

```
model 38: //four analog channels plus base sign diff [size 8] (Stair Stepping MODEL)
    tlex[0]=(Sg*a); //force along gravity vector
    twg=(sg*w); //rotation along gravity vector (heading change);
    tlex[1]=(a-Sg*tlex[0]). Mag( )//forces perpendicular to gravity vector
    tlex[2]=(w-Sg*twg). Mag( )//rotation perpendicular to gravity vector (heading change);
    tlex[3]=alt; //adjusted barometric altitude sensor data
    //assign 4 raw channels
    for (i=0; i<3; i++)
        lex[i]=tlex[i+4]=tlex[i];
    //apply differential sign of each channel
    for (i=4; i<8; i++)
    {
        lex[i]=(tlex[i]>m_prev[i]?1: -1);
        m_prev[i]=tlex[i];
    }
```
© 2015 Yotta Navigation Corporation The inputs to the model, in embodiments, are as follows:
From the MARG IMU:
vector a (a[0],a[1],a[2]); filtered platform frame acceleration sensor data (scaled to gravity)
Vector w (w[0],w[1],w[2]); filtered platform frame rate gyro sensor data (rad/s)
Where vectors a and w are time box car smoothed values depending on the model 's' parameters implementation. In most model implementations, smoothing is not used (set to 1, e.g. s1=no smoothing)
From the Attitude EKF:
Vector Sg (sg[0],Sg[1],Sg[2]); Platform EKF attitude gravity vector (normalized) (earth frame)
vector Sm (Sm[0],Sm[1],Sm[2]); Platform EKF attitude magnetic vector (normalized) (earth frame)
From the Walk Model Attitude:
Vector walkU (walkU[0], walkU[1], walkU[2]); Body frame UP determined from WALK model
vector walkL (walkL[0], walkL[1], walkL[2]); Body frame LEFT determined from WALK model
Vector walkF (walkF[0], walkF[1], walkF[2]); Body frame FORWARD determined from WALK model
Feature vectors are described by lex: an array of <float>. Array size is model dependent. Note that lex[0] is always used for triggering when the model is event driven.

Some further examples of models utilized for identifying human motions, according to embodiments, are:
Walking Backwards:
_Back.1234abcd-20150126-173418.m30_s1_t-2_w40_J80-modified.M1K25R2.T80.MODLow
Crawling:
_Crawl.1234abcd-20141208-222834.m34_s1_t20_w40_J80-modified.M1_K25_R2.T80.MOD
Jogging:
_Jog.1234abcd-20141208-175437.m27_s1_t-2_w40_J40-modified.M1_K25_R2.T40.MOD
Jumping:
_Jump.1234abcd-20141208-214748.m29_s1_t-2_w10_J10-modified.M1_K2_R2.T10.MOD
Roll Backwards:
_RollBackward.1234abcd-20141208-215514.m26 s1_t-2_w40_f40.M1_K2_R1.T40.MOD
Roll Forwards:
_RollForward.1234abcd-20141208-215514.m26_S1_t-2_w40_J40.M1_K2_R1.T40.MOD
Lateral Roll Left
_RollLeft.1234abcd-20141208-215514.m26 s1_t-2_w40_f40.M1_K2_R1.T40.MOD
Lateral Roll Right
_RollRight.1234abcd-20141208-215514.m26_S1_t-2_w40_J40.M1_K2_R1.T40.MOD
Run:
_Run.1234abcd-20141209-213753.m27_s1_t-2_w20_f40-modified.M1_K25_R2.T40.MOD
Side Step Left:
_SideLeft.1234abcd-20150128-201649.m35 s3_t20_w40_f80-modified.M1_K25_R2.T80.MOD
Side Step Right:
_SideRight.1234abcd-20141208-184324.m35_s3_t20_w40_J80-modified.M1_K25_R2.T80.MOD
Spin Left: anticlockwise spin
_SpinLeft.1234abcd-20141208-215514.m26_s1_t-2_w40_J40.M1_K2_R1.T40.MOD
Spin Right:clockwise spin
_SpinRight.1234abcd-20141208-215226.m26_s1_t-2_w40_f40.M1_K2_R1.T40.MOD
Walking Forwards:
_Walk.1234abcd-20141208-173850.m27_s1_t-2_w40_J80.M1_K25_R2.T80.MOD
Stair Stepping Up:
_SSUp.1234abcd-20150126-173418.m38_s2_t-2_w40_J80-modified.M1_K25_R2.T80.MOD
Stair Stepping Down:
_SSDown.1234abcd-20150126-173418.m38 s2_t-2_w40_f80-modified.M1_K25_R2.T80.MOD
StandingUp:
_SSUp.1234abcd-20150126-173418.m27_s1_c2_t10_w20_J50-modified.M1_K20_R2.T50.MOD
SittingDown:
_SSDown.1234abcd-20150126-173418.m27_s1_10_w20_f50-modified.M1_K25_R0.T50.MOD In further embodiments, the following model is an example of a model that may be used as an alternative for identifying walking backwards:
Walking Backwards:
_Back.1234abcd-20141208-202604.m36_s3_t20_w40_f80-modified.M1_K25_112.T80.MOD The limitation of inputs to specific inputs used in the models described herein is important for the optimized functioning of the models within the IHM systems described herein for the identification of specific human motions. In other words, the absence of a specific input to a model is to be viewed herein as an express exclusion of the unnamed inputs.

Examples of 38 models (including the walk model 27) are provided in FIGS. 5A-5D.

The system described herein may be implemented on a computer system within which a set of instructions for causing the system to perform any one of the foregoing methodologies and process flows may be executed. In alternative embodiments, the system may comprise a network router, a network switch, a network bridge, personal digital assistant (PDA), a cellular telephone, a Web appliance or any system capable of executing a sequence of instructions that specify actions to be taken by that system.

The computer system may include a processor, a main memory and a static memory, which communicate with each other via a bus. The computer system may further include a display unit, for example, a liquid crystal display. The computer system may also include an alphanumeric input device, for example, a keyboard or a touch screen; a cursor control device, for example, a mouse; a disk drive unit; a signal generation device, for example, a speaker; etc.

Data may be provided to the computer system on a computer readable data storage device, such as read-only memory (ROM); random access memory (RAM); magnetic disk storage media; optical storage media; and flash memory devices. Furthermore, data may be stored in the cloud, or another remote computer readable memory device and provided to the computer system through a network interface device.

The systems includes a machine-readable medium on which is stored a set of executable instructions, i.e. software, embodying any one, or all, of the methodologies and process flows described herein. The software may also in embodiments reside, completely or at least partially, within the main computer memory and/or within the processor. The software may further be transmitted or received over a network by means of a network interface device.

A dedicated data memory unit may be utilized for storing one or more of the IHM Model Database, IHM Event Database, IHM Dead Reckoning Database, IHM Event Log, Dead Reckoning/GPS Calibration Parameters, etc. The dedicated data memory may include any mechanism for storing information in a form readable by a machine, e.g. a computer, including read-only memory (ROM); random access memory (RAM); magnetic disk storage media; optical storage media; and flash memory devices. Furthermore, in embodiments data storage may be in the cloud.

Furthermore, in embodiments logic circuitry may be used instead of computer-executed instructions to implement processing. Depending upon the particular requirements of the application in the areas of speed, expense, tooling costs, and the like, this logic may be implemented by constructing an ASIC having thousands of tiny integrated transistors. Such an ASIC may be implemented with CMOS (complementary metal oxide semiconductor), TTL (transistor-transistor logic), VLSI (very large systems integration), or another suitable construction. Other alternatives include a digital signal processing chip (DSP), discrete circuitry (such as resistors, capacitors, diodes, inductors, and transistors), field programmable gate array (FPGA), programmable logic array (PLA), programmable logic device (PLD), and the like.

It is to be understood that embodiments may be used as or to support software programs or software modules executed upon some form of processing core (such as the CPU of a computer) or otherwise implemented or realized upon or within a system or computer readable medium. A machine-readable medium includes any mechanism for storing or transmitting information in a form readable by a machine, e.g. a computer. For example, a machine readable medium includes read-only memory (ROM); random access memory (RAM); magnetic disk storage media; optical storage media; flash memory devices; electrical, optical, acoustical or other forms of propagated signals, for example, carrier waves, infrared signals, digital signals, etc.; or any other type of media suitable for storing or transmitting information.

Further, it is to be understood that embodiments may include performing operations and using storage with cloud computing. For the purposes of discussion herein, cloud computing may mean executing software instructions on any network that is accessible by Internet-enabled or network-enabled devices, servers, or clients and that do not require complex hardware configurations, e.g. requiring cables and complex software configurations. For example, embodiments may provide one or more cloud computing solutions that enable users to obtain compositional data, including images, etc. without user involvement on such internet-enabled or other network-enabled devices, servers, or clients. It further should be appreciated that one or more cloud computing embodiments may include using mobile devices, tablets, and the like.

Although embodiments of the present invention have been particularly described with reference to a single sensor platform attached to a subject, the principles and teaching of the present invention may be applied to systems in which two or more sensor platforms are attached to the subject, all supplying data for processing together to identify more complex human motions. For example, sensor platforms may be usefully attached to arms, legs, trunk and/or head of a subject for the purpose of identifying correctly performed martial arts moves, a correctly executed golf swing, etc. IHM feature construction would proceed as described above, simply with a larger set of input data—the combined data from the multiple sensor platforms—ultimately resulting in IHM feature models that could be used to efficiently identify more complex human motions.

Although described with reference to the preferred embodiments thereof, it will be readily apparent to those of ordinary skill in the art that modifications in the form and details of the disclosed embodiments can be made without departing from the spirit and scope thereof. Further, embodiments disclosed herein may include various operations as set forth above, or fewer or more operations; or operations in an order different from the order described. Accordingly, the scope should be judged in terms of the claims which follow as well as the legal equivalents thereof

What is claimed is:

1. A system for identifying human motion of a subject, comprising:
   a sensor platform attached to said subject, said sensor platform comprising 3-axis magnetometers, 3 axis accelerometers, 3-axis rate gyroscopes and a first memory for storing time synchronized magnetometer, accelerometer and rate gyroscope data at sample times separated by a specified time interval;
   an attitude filter that receives said magnetometer, accelerometer and rate gyroscope data from said sensor platform, said attitude filter comprising a processor programmed to calculate, from said magnetometer, accelerometer and rate gyroscope data, attitude and heading of said sensor platform at each of said sample times;
   a feature construction and aggregation unit that receives said magnetometer, accelerometer and rate gyroscope data from said sensor platform and said attitude and heading from said attitude filter, said feature construction and aggregation unit comprising a processor programmed to calculate a feature vector for a human motion model from said magnetometer, accelerometer, and rate gyroscope data and said attitude and heading, using a predefined template stored in a second memory, a feature vector being calculated for each of said sample times, feature vectors for a specified number of consecutive sample times being aggregated into a frame, a plurality of said frames being generated; and an evaluation unit that receives said plurality of said frames, said evaluation unit being programmed to calculate the probability, for each one of said frames, that said feature vectors in said frame resulted from an instance of a specific human motion corresponding to said human motion model;

wherein said human motion model is a model chosen from the group consisting of walking forwards, jogging and running, and said specific human motion is correspondingly walking forwards, jogging and running, respectively;

wherein said feature vector comprises:
- a first feature construction being force, u, along the gravity field direction;
- a second feature construction being a magnitude, v, of forces perpendicular to the gravity field direction;
- a third feature construction being a magnitude, w, of rotations perpendicular to the gravity field direction;
- a fourth feature construction being a function, V(du/dt), where du/dt is a time derivative of said force along the gravity field direction;
- a fifth feature construction being a function, V(dv/dt), where dv/dt is a time derivative of said magnitude of forces perpendicular to the gravity field direction; and
- a sixth feature construction being a function, V(dw/dt), where dw/dt is a time derivative of said magnitude of rotations perpendicular to the gravity field direction;

wherein:
V(x)=2*H(x)−1, and H(x) is the Heaviside step function,
H(x)=+1 (x>0), 0 (x<0).

2. The system as in claim 1, wherein said feature vector consists of said first feature construction, said second feature construction, said third feature construction, said fourth feature construction, said fifth feature construction and said sixth feature construction.

3. The system as in claim 1, wherein said evaluation unit is programmed to use a factorial hidden Markov model.

4. The system as in claim 1, wherein said evaluation unit is programmed to use a hidden Markov model.

5. The system as in claim 1, wherein said sensor platform is attached to the torso of said subject.

6. The system as in claim 1, wherein said sensor platform is securely attached to said subject, said sensor platform not moving relative to the part of said subject where said sensor platform is attached.

7. The system as in claim 5, wherein said sensor platform is strapped to the torso of said subject.

8. The system as in claim 1, wherein said attitude filter comprises an extended Kalman filter.

9. The system as in claim 1, wherein each one of said frames comprises feature vectors covering a time period of approximately two seconds.

10. A method of identifying human motion of a subject, comprising:

acquiring time synchronized magnetometer, accelerometer and rate gyroscope data at sample times separated by a specified time interval using a sensor platform attached to said subject, said sensor platform comprising 3-axis magnetometers, 3 axis accelerometers, 3-axis rate gyroscopes and a first memory for storing said time synchronized magnetometer, accelerometer and rate gyroscope data;

calculating attitude and heading of said sensor platform at each of said sample times at an attitude filter unit comprising a filter and a processor, by manipulating said magnetometer, accelerometer and rate gyroscope data received from said memory;

calculating a feature vector for a human motion model at a feature construction and aggregation unit comprising a processor programmed to calculate said feature vector for a walking forwards model from said magnetometer, accelerometer, and rate gyroscope data received from said first memory and said attitude and heading received from said attitude filter unit, using a predefined template stored in a second memory, a feature vector being calculated for each of said sample times, feature vectors for a specified number of consecutive sample times being aggregated into a frame, a plurality of said frames being generated; and calculating the probability, at an evaluation unit, for each one of said plurality of said frames, that said feature vectors in said frame resulted from an instance of a specific human motion corresponding to said human motion model;

wherein said human motion model is a model chosen from the group consisting of walking forwards, jogging and running, and said specific human motion is correspondingly walking forwards, jogging and running, respectively;

wherein said feature vector comprises:
- a first feature construction being force, u, along the gravity field direction;
- a second feature construction being a magnitude, v, of forces perpendicular to the gravity field direction;
- a third feature construction being a magnitude, w, of rotations perpendicular to the gravity field direction;
- a fourth feature construction being a function, V(du/dt), where du/dt is a time derivative of said force along the gravity field direction;
- a fifth feature construction being a function, V(dv/dt), where dv/dt is a time derivative of said magnitude of forces perpendicular to the gravity field direction; and
- a sixth feature construction being a function, V(dw/dt), where dw/dt is a time derivative of said magnitude of rotations perpendicular to the gravity field direction;

wherein:
V(x)=2*H(x)−1, and H(x) is the Heaviside step function,
H(x)=+1 (x>0), 0 (x<0).

11. The method of claim 10, wherein said feature vector consists of said first feature construction, said second feature construction, said third feature construction, said fourth feature construction, said fifth feature construction and said sixth feature construction.

12. The method of claim 10, wherein said evaluation unit is programmed to use a factorial hidden Markov model.

13. The method of claim 10, wherein said evaluation unit is programmed to use a hidden Markov model.

14. The method of claim 10, wherein said sensor platform is attached to the torso of said subject.

15. The method of claim 10, wherein said sensor platform is securely attached to said subject, said sensor platform not moving relative to the part of said subject where said sensor platform is attached.

16. The method of claim 10, wherein said sensor platform is strapped to the torso of said subject.

17. The method of claim 10, wherein said attitude filter comprises an extended Kalman filter.

18. The method of claim 10, wherein each one of said frames comprises feature vectors covering a time period of approximately two seconds.

19. A dead reckoning system for a human subject travelling on foot, comprising:
- said system of claim 1 for identifying human motion of walking forwards of a subject;
- an event processing unit that receives said probability, for each one of said frames, that said feature vectors in the frame resulted from an instance of walking forwards from said evaluation unit, said event processing unit comprising a processor programmed to qualify a walking forwards event;
- a GPS event unit that receives GPS positional data, said GPS event unit comprising a processor programmed to calculate the position of said dead reckoning system from said GPS positional data;
- a database unit comprising a memory device, said database unit storing subject parameters, said subject parameters comprising an average step length of said subject, and GPS positional data received from said GPS event unit; and
- a navigation update unit that receives notification of qualified walking forwards events and retrieves subject parameters and GPS positional data from said database unit, said navigation update unit comprising a processor programmed to calculate a navigation update relative to a last known position determined by said GPS positional data.

20. The dead reckoning system of claim 19, wherein said qualifying a walking forwards event comprises applying a Bayesian normalization to multiple unqualified events identified within a predetermined period of time.

21. The dead reckoning system of claim 19, further comprising a display that receives said navigation updates and displays said navigation updates on a map.

22. The dead reckoning system of claim 19, further comprising a wireless transmitter for transmitting said navigation updates to another device.

23. A system for identifying human motion of a subject, comprising:
- a sensor platform attached to said subject, said sensor platform comprising 3-axis magnetometers, 3 axis accelerometers, 3-axis rate gyroscopes and a first memory for storing time synchronized magnetometer, accelerometer and rate gyroscope data at sample times separated by a specified time interval;
- an attitude filter that receives said magnetometer, accelerometer and rate gyroscope data from said sensor platform, said attitude filter comprising a processor programmed to calculate, from said magnetometer, accelerometer and rate gyroscope data, attitude and heading of said sensor platform at each of said sample times;
- a feature construction and aggregation unit that receives said magnetometer, accelerometer and rate gyroscope data from said sensor platform and said attitude and heading from said attitude filter, said feature construction and aggregation unit comprising a processor programmed to calculate a feature vector for a human motion model from said magnetometer, accelerometer, and rate gyroscope data and said attitude and heading, using a predefined template stored in a second memory, a feature vector being calculated for each of said sample times, feature vectors for a specified number of consecutive sample times being aggregated into a frame, a plurality of said frames being generated; and
- an evaluation unit that receives said plurality of said frames, said evaluation unit being programmed to calculate the probability, for each one of said frames, that said feature vectors in said frame resulted from an instance of a specific human motion corresponding to said human motion model;

wherein said human motion model is a model chosen from the group consisting of walking forwards, jogging, running, side stepping left, side stepping right, walking backwards, standing up, sitting down and traversing stairs, and said specific human motion is correspondingly walking forwards, jogging, running, side stepping left, side stepping right, walking backwards, standing up, sitting down and traversing stairs, respectively;

wherein said feature vector comprises:
- one or more first feature constructions, X, comprising at least one of:
  - a force along the gravity field direction;
  - a magnitude of forces perpendicular to the gravity field direction;
  - a magnitude of rotations perpendicular to the gravity field direction; and
  - an adjusted pressure altitude;
- one or more second feature constructions which are derivatives dX/dt, wherein dX/dt is a time derivative of one of said one or more feature constructions X; and
- one or more third feature constructions which are derivatives V(dX/dt), wherein:
  - V(x)=2*H(x)−1, and H(x) is the Heaviside step function,
  - H(x)=+1 (x>0), 0 (x<0), and x is dX/dt.

24. A system for identifying human motion of walking forwards of a subject, comprising:
- a sensor platform attached to said subject, said sensor platform comprising 3-axis magnetometers, 3 axis accelerometers, 3-axis rate gyroscopes and a memory for storing time synchronized magnetometer, accelerometer and rate gyroscope data at sample times separated by a specified time interval;
- an attitude filter that receives said magnetometer, accelerometer and rate gyroscope data from said sensor platform, said attitude filter comprising a processor programmed to calculate, from said magnetometer, accelerometer and rate gyroscope data, attitude and heading of said sensor platform at each of said sample times;
- a feature construction unit that receives said magnetometer, accelerometer and rate gyroscope data from said sensor platform and said attitude and heading from said attitude filter, said feature construction unit comprising a processor programmed to calculate feature vectors for each of said sample times for a walking forwards human motion model from said magnetometer, accelerometer, and rate gyroscope data and said attitude and heading; and
- an evaluation unit that receives said feature vectors, said evaluation unit being programmed to calculate the probability that said feature vectors resulted from an instance of said human motion of walking forwards;

wherein each of said feature vectors comprise:
one or more first feature constructions, X, comprising:
a force along the gravity field direction;
a magnitude of forces perpendicular to the gravity field direction; and
a magnitude of rotations perpendicular to the gravity field direction;
one or more second feature constructions which are derivatives dX/dt, wherein dX/dt is a time derivative of one of said one or more feature constructions X; and
one or more third feature constructions which are derivatives V(dX/dt), wherein:
V(x)=2*H(x)−1, and H(x) is the Heaviside step function,
H(x)=+1 (x>0), 0 (x<0), and x is dX/dt.

* * * * *